(12) United States Patent
Hodges et al.

(10) Patent No.: US 12,016,636 B2
(45) Date of Patent: Jun. 25, 2024

(54) SYSTEM AND METHOD OF TRACTOGRAPHY LABELING IN THE PRESENCE OF BRAIN LESION

(71) Applicant: SYNAPTIVE MEDICAL INC., Toronto (CA)

(72) Inventors: Wes Hodges, London (CA); Alicia McNeely, Toronto (CA)

(73) Assignee: Synaptive Medical Inc.

( * ) Notice: Subject to any disclaimer, the term of this patent is extended or adjusted under 35 U.S.C. 154(b) by 294 days.

(21) Appl. No.: 17/653,328

(22) Filed: Mar. 3, 2022

(65) Prior Publication Data

US 2022/0280239 A1 Sep. 8, 2022

Related U.S. Application Data

(63) Continuation-in-part of application No. 17/502,278, filed on Oct. 15, 2021, now Pat. No. 11,355,230.

(Continued)

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/25* (2016.02); *A61B 90/37* (2016.02); *G16H 20/40* (2018.01);
(Continued)

(58) Field of Classification Search
CPC ... A61B 34/10; A61B 34/25; A61B 2034/102; A61B 2034/107; A61B 2034/258; A61B 2034/374; A61B 90/37; G16H 20/40
See application file for complete search history.

(56) References Cited

U.S. PATENT DOCUMENTS

2015/0310652 A1* 10/2015 Dobson ................... G06T 11/60
345/629
2016/0005169 A1* 1/2016 Sela ..................... A61B 5/0066
382/131

OTHER PUBLICATIONS

Hodges et al., "System and Method of Selectively Showing Tractography in Areas Containing Free Water", U.S. Appl. No. 17/502,278, filed Oct. 15, 2021.

* cited by examiner

Primary Examiner — Chao Sheng

(57) ABSTRACT

A system and methods for labeling tractography, having a tract segmentation and a tract labeling atlas, in a presence of a lesion in a brain, involving: a graphical user interface (GUI) comprising a tool configured to facilitate adjusting a displacement for intraoperatively reperforming the tract segmentation in approximately real time, modeling deformation of the tract labeling atlas by facilitating modeling a force exerted by the lesion on the brain, and defining parameters of a size, a shape, and a level of the displacement condition; and a processor in communication with the GUI and configured to: determine whether an infiltration condition and a displacement condition appears in the tractography; if the infiltration condition and the displacement condition is determined to appear in the tractography, estimate the infiltration condition and the displacement condition; if the displacement condition is determined to appear in the tractography, instruct the GUI to render the tool and model the force exerted by the lesion on the brain by using the parameters, whereby a new tract segmentation and a new tract labeling atlas are provided; and if the displacement condition is determined to be absent from the tractography, refrain from modeling the force, a presence of only the infiltration condition being assumed.

20 Claims, 14 Drawing Sheets

Related U.S. Application Data

(60) Provisional application No. 63/161,585, filed on Mar. 16, 2021, provisional application No. 63/155,898, filed on Mar. 3, 2021.

(51) Int. Cl.
*A61B 90/00* (2016.01)
*G16H 20/40* (2018.01)

(52) U.S. Cl.
CPC ... *A61B 2034/102* (2016.02); *A61B 2034/107* (2016.02); *A61B 2034/258* (2016.02); *A61B 2090/374* (2016.02)

SYSTEM AND METHOD OF TRACTOGRAPHY LABELING IN THE PRESENCE OF BRAIN LESION

CROSS-REFERENCE TO RELATED APPLICATION(S)

This document is a nonprovisional application claiming the benefit of, and priority to, U.S. Provisional Patent Application Ser. No. 63/155,898, entitled "System and Method of Tractography Labeling in the Presence of Brain Lesion," filed on Mar. 3, 2021, U.S. Nonprovisional patent application Ser. No. 17/502,278, entitled "System and Method for Selectively Showing Tractography in Areas Containing Free Water," filed on Oct. 15, 2021, and U.S. Provisional Patent Application Ser. No. 63/161,585, entitled "SYSTEM AND METHOD OF TRACTOGRAPHY LABELING IN THE PRESENCE OF BRAIN LESION," filed Mar. 16, 2021, all of which are hereby incorporated by reference herein in their entirety.

FIELD

Generally, the present disclosure relates to surgical planning. More specifically, the present disclosure relates to surgical planning for neurosurgery. Even more specifically, the present disclosure relates to labeling tractography from surgical planning data.

BACKGROUND

In the related art, tractography is used for subjective surgical decision making. In particular, surgeons visualize tractography, relative to a surgical trajectory, to inform the path of least destruction to the white matter. Different white matter fibers have an anatomical location in a human brain and transmit different pieces of information. For example, corticospinal tracts transmit motor signals; and the arcuate fibers transmit language signals. As such, tracts, representing these white matter fibers, can be labelled as to which anatomical fiber bundle these white matter fibers belong.

However, in the presence of pathology, i.e., a lesion, the fiber anatomy is locally changed. Some lesions (typically primary cancers) grow within the white matter itself and are referred to as an infiltrative disease or infiltration, wherein the fiber anatomy is cut by the lesion. Other lesions (typically secondary cancers) grow in between the fibers, and, like edema, wherein the lesion pinches the fiber anatomy and/or displaces the fiber anatomy to other areas of the brain which is referred to as a mass effect or displacement.

Both types of effect (infiltration or displacement) change how an automated, atlas-based tract labeling algorithm should behave. In the case of infiltration, a labeling algorithm should expect to find a reduced number of tracts in the area of pathology. In the case of displacement, a labeling algorithm should locally deform its atlas based on the size and shape of the lesion to obtain a more accurate labeling result.

While labeling could be corrected manually, clinicians simply do not have the time to invest in doing that, and instead, work around these errors. Minimizing or eliminating these errors provides them with a more complete image of the patient's current anatomy, and would increase their confidence in the data and their approach. There is a desire to differentiate tract infiltration versus displacement within the edematous region identified by free water correction to locally deform the segmentation atlas prior to tract labeling.

In neuroscience, tractography is a 3D modeling technique that is used for subjective surgical decision-making by visually representing nerve fibers (neural tracts) using data collected by diffusion magnetic resonance imaging (MRI). The results of tractography are presented in two-dimensional (2D) images and three-dimensional (3D) images referred to as tractograms, whereby surgeons use the tractograms to choose a surgical trajectory having a path of least destruction to white matter, i.e., matter containing nerve tracts in the deeper tissues of the brain (subcortical), which are surrounded by a white myelin sheath or covering. Related art tractography algorithms can produce 90% of nerve tracts, but are confounded by the presence of edema (swelling) caused by an extracellular fluid that can move in any direction, referred to as "isotropic free water." This isotropic free water hides anisotropic water, i.e., corresponding to the neural tracts, during magnetic resonance imaging (MRI).

In the related art, some methods for subtracting a signal corresponding to the free water from an MRI signal so as not to occlude a desired neural tract are referred to as free water correction (FWC) algorithms. Such FWC algorithms include, for example, those described in Fraser Henderson Jr., M.D., Drew Parker, BSc, Anupa A. Vijayakumari, PhD, Mark Elliott, PhD, Timothy Lucas, MD, PhD, Michael L. McGarvey, MD, Lauren Karpf, BSc, Lisa Desiderio, RT, Jessica Harsch, BSc, Scott Levy, BSc, Eileen Maloney-Wilensky, N P, Ronald L. Wolf, MD, PhD, Wesley B. Hodges, BASc, Steven Brem, MD, Ragini Verma, PhD, "Enhanced Fiber Tractography Using Edema Correction: Application and Evaluation in High-Grade Gliomas," NEUROSURGERY, Vol. 0, No. 0 (2021), hereinafter Henderson, et al.

Currently, pathology causes many complexities for tract labeling. Related art approaches all suffer from incorrect tract labeling corresponding to a diseased area of the brain. Since different pathologies, such as glioblastomas and brain metastases, present free water differently, MRI images of neural tracts in the presence of different pathologies may be subjected to different degrees of occlusion based on free water content. Further related art technologies are incapable of pathology modeling to locally modify an atlas for tract labeling. Thus, a long-felt need exists in the related art for addressing challenges in tractography when displaying non-pathological free water areas and different pathological areas as well as in labeling tractography in different pathological areas.

SUMMARY

In addressing at least some of the challenges in the related art, a system and methods of labeling tractography in the presence of a brain lesion are provided, in accordance with embodiments of the present disclosure. While accounting for at least one of an infiltration and a displacement in relation to tractography, the system and the methods of the present disclosure involve an initial estimation of at least one of the infiltration and the displacement as well as the provision of a user interface (UI), e.g., to a user, for facilitating adjusting at least one of an infiltration level and a displacement level to intraoperatively re-perform a tract segmentation in at least near real-time. The UI comprises a graphical user interface (GUI). The GUI comprises a tool, such as a software tool, e.g., a slider tool, operable in relation to data from surgical planning software. The system and the methods of the present disclosure involve a semi-automated approach comprising automating approximately 80% of the labeling work and providing a tool configured with fine control to facilitate manual operation by facilitating approximately 20% of the labeling work, thereby saving clinical time.

In general, the system and the methods of the present disclosure further involve modeling a force that a lesion would exert on a brain by differentiating an infiltration from a displacement within an edematous region that is identified by FWC algorithm to locally deform a segmentation atlas prior to labeling a tract. The tool facilitates modeling a force that a lesion would exert on a brain by facilitating locally deforming a tract labeling atlas, relating to a tractography, in a 3D space. This force is modeled by using a size, a shape, and a displacement level as defined by the tool, e.g., a slider feature having a slider. As a level of displacement increases, the force increases. In the case of purely infiltrative disease, e.g., no displacement occurring, then no force is modeled, and the atlas is not deformed. Furthermore, the labeling expects fewer tracts in the edematous region and takes steps to label neural tracts, accordingly, including labeling tracts in that area as belonging to the pathology itself.

In accordance with some embodiments of the present disclosure, an MRI user interface system for labeling tractography from surgical planning data in a presence of a lesion in a brain, the tractography comprising a tract segmentation and a tract labeling atlas in relation to a three-dimensional space, comprises: a graphical user interface (GUI) comprising a tool, the tool configured to facilitate: adjusting a displacement for intraoperatively reperforming the tract segmentation in approximately real time, modeling deformation of the tract labeling atlas by facilitating modeling a force exerted by the lesion on the brain, and defining at least one parameter of a size, a shape, and a level of the displacement condition; and a processor in communication with the GUI and configured, by a set of executable instructions storable in relation to a non-transient memory device, to: determine whether at least one of an infiltration condition and a displacement condition appears in the tractography; if at least one of the infiltration condition and the displacement condition is determined to appear in the tractography, estimate the at least one of the infiltration condition and the displacement condition; if the displacement condition is determined to appear in the tractography, instruct the GUI to render the tool and model the force exerted by the lesion on the brain by using the at least one parameter, whereby a new tract segmentation and a new tract labeling atlas are provided; and if the displacement condition is determined to be absent from the tractography, refrain from modeling the force, wherein a presence of only the infiltration condition is assumed.

In accordance with some embodiments of the present disclosure, a method of providing an MRI user interface system for labeling tractography from surgical planning data in a presence of a lesion in a brain, the tractography comprising a tract segmentation and a tract labeling atlas in relation to a three-dimensional space, comprises: providing a graphical user interface (GUI), providing the GUI comprising providing a tool, providing the tool comprising configuring the tool to facilitate: adjusting a displacement for intraoperatively reperforming the tract segmentation in approximately real time, modeling deformation of the tract labeling atlas by facilitating modeling a force exerted by the lesion on the brain, and defining at least one parameter of a size, a shape, and a level of the displacement condition; and providing a processor in communication with the GUI, providing the processor comprising configuring the processor, by a set of executable instructions storable in relation to a non-transient memory device, to: determine whether at least one of an infiltration condition and a displacement condition appears in the tractography; if at least one of the infiltration condition and the displacement condition is determined to appear in the tractography, estimate the at least one of the infiltration condition and the displacement condition; if the displacement condition is determined to appear in the tractography, instruct the GUI to render the tool and model the force exerted by the lesion on the brain by using the at least one parameter, whereby a new tract segmentation and a new tract labeling atlas are provided; and if the displacement condition is determined to be absent from the tractography, refrain from modeling the force, wherein a presence of only the infiltration condition is assumed.

In accordance with some embodiments of the present disclosure, a method of labeling tractography from surgical planning data in a presence of a lesion in a brain, the tractography comprising a tract segmentation and a tract labeling atlas in relation to a three-dimensional space by way of an MRI user interface system, comprises: providing the MRI user interface system, providing the MRI user interface system comprising: providing a graphical user interface (GUI), providing the GUI comprising providing a tool, providing the tool comprising configuring the tool to facilitate: adjusting a displacement for intraoperatively reperforming the tract segmentation in approximately real time, modeling deformation of the tract labeling atlas by facilitating modeling a force exerted by the lesion on the brain, and defining at least one parameter of a size, a shape, and a level of the displacement condition; and providing a processor in communication with the GUI, providing the processor comprising configuring the processor, by a set of executable instructions storable in relation to a non-transient memory device, to: determine whether at least one of an infiltration condition and a displacement condition appears in the tractography; if at least one of the infiltration condition and the displacement condition is determined to appear in the tractography, estimate the at least one of the infiltration condition and the displacement condition; if the displacement condition is determined to appear in the tractography, instruct the GUI to render the tool and model the force exerted by the lesion on the brain by using the at least one parameter, whereby a new tract segmentation and a new tract labeling atlas are provided; and if the displacement condition is determined to be absent from the tractography, refrain from modeling the force, wherein a presence of only the infiltration condition is assumed; and operating the MRI user interface system.

In some embodiments of the present disclosure, a system and methods involve selectively displaying free water in tractography. In one aspect, free water data and post-processed tract data are combined into a single tractography set with a "degree of free water" value being assigned to a geometry for each neural tract and/or a geometry for each fragment of a neural tract, such as neural tract segments and/or points. A tool, comprising a slider is configured to facilitate dynamically adjusting a free water threshold value for controlling display of at least one of a geometry for each neural tract and a geometry for each fragment of a neural tract. For example, only a geometry for each neural tract and a geometry for each fragment of a neural tract, corresponding to a degree of free water below a threshold value is displayed while other geometry is hidden.

According to an aspect, a method is provided for selectively displaying free water in tractography, comprising: applying a free water correction algorithm to an MRI image and assigning degree of free water values, which can be actual estimated percentages of free water or other metrics related to free water content, to each tract and/or fragment of tract geometry in the MRI image; comparing the degree of free water values to a threshold indicated by a slider interface; and refreshing the MRI image so that only those tracts and/or fragments of tract geometry having degree of free water values less than or equal to the threshold are displayed, while others are hidden.

According to another aspect, a system is provided for selectively displaying free water in tractography, comprising: an MRI system for generating an MRI image, the MRI system including a data processing system for applying a free water correction algorithm to the MRI image and assigning degree of free water values to each tract and/or fragment of tract geometry in the MRI image; a graphical user interface having a first area for displaying the MRI image, and a second area with user interface elements for controlling aspects of the MRI image displayed in the first area; a free water correction slider interface in the second area for indicating a threshold of free water, in response to which the MRI system compares the degree of free water values to the threshold indicated by the slider interface and refreshes the MRI image so that only those tracts and/or fragments of tract geometry having degree of free water values less than or equal to the threshold are displayed, while others are hidden.

The details of one or more aspects of the subject matter of the present disclosure are set forth in the accompanying drawings and the below description. Other features, aspects, and advantages of the subject matter will become apparent from the description, the drawings, and the claims.

BRIEF DESCRIPTION OF THE DRAWINGS

The above and other aspects, features, and advantages of several embodiments of the present disclosure will be more apparent from the following Detailed Description as presented in conjunction with the following several figures of the Drawing.

Figure 1:
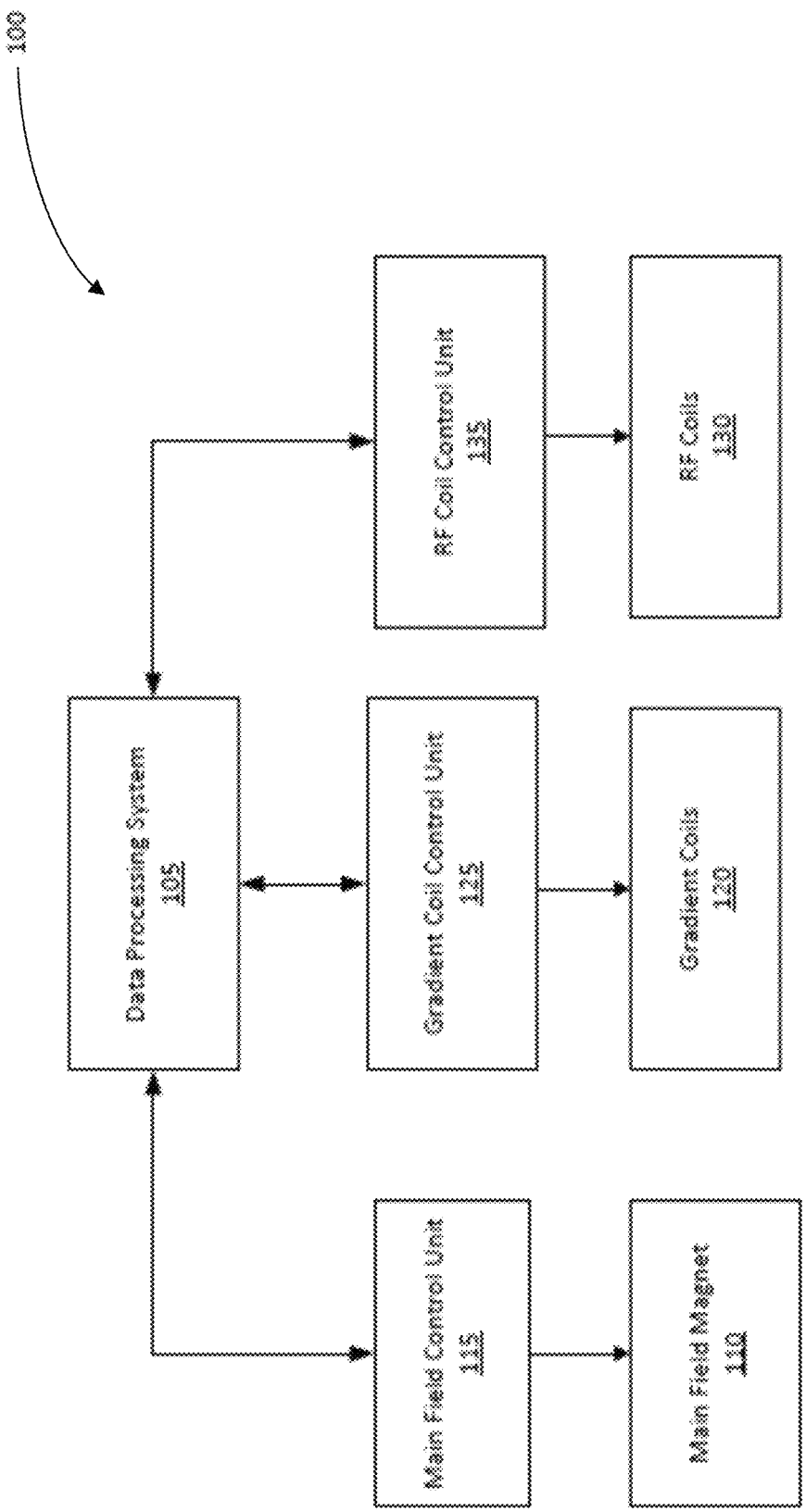
FIG. 1 is a block diagram illustrating functional subsystems of an MRI system.

Corresponding reference numerals or characters indicate corresponding components throughout the several figures of the Drawing(s). Elements in the several figures are illustrated for simplicity and clarity and have not necessarily been drawn to scale. For example, the dimensions of some elements in the several figures may be emphasized relative to other elements for facilitating understanding of the various presently disclosed embodiments. Also, common, but well-understood, elements that are useful or necessary in commercially feasible embodiment are often not depicted to facilitate a less obstructed view of these various embodiments of the present disclosure.

DETAILED DESCRIPTION

Various embodiments, features, and aspects of the present disclosure are below described with reference to details. The following detailed description and the drawings are illustrative of the present disclosure and are not to be construed as limiting the present disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" as well as variations thereof denote the specified features, steps, or components are included. These terms are not to be interpreted to exclude the presence of other features, steps, or components.

As used herein, the term "exemplary" denotes "serving as an example, instance, or illustration" and should not be construed as preferred or advantageous over other configurations herein disclosed. As used herein, the terms "about" and "approximately" are intended to cover variations that may exist in the upper and lower limits of the ranges of values, such as variations in properties, parameters, and dimensions. In one non-limiting example, the terms "about" and "approximately" denote plus or minus 10 percent or less.

As used herein, the term "determining" encompasses a wide variety of actions; therefore, "determining" includes, but is not limited to, calculating, computing, processing, deriving, investigating, ascertaining, searching, looking-up, e.g., looking-up data or any other information in a table, a database, or another data structure, and the like. Also, "determining" includes, but is not limited to, receiving, e.g., receiving information, accessing, e.g., accessing data in a memory, and the like. Further, "determining" includes, but is not limited to, resolving, selecting, choosing, establishing, and the like. As used herein, the phrase "based on" does not denote "based only on," unless otherwise expressly specified. In other words, the phrase "based on" denotes both "based only on" as well as "based at least on."

As described herein, functions of any features of any embodiment of the present disclosure may be stored as one or more instructions on at least one of a processor-readable medium and a computer-readable medium. The term "computer-readable medium" denotes any available medium that is accessible by a computer or processor. By way of example, and not limitation, such a medium may comprise RAM, ROM, EEPROM, flash memory, CD-ROM or other optical disk storage, magnetic disk storage, or other magnetic storage devices, or any other medium, including a cloud server, that is usable for storing desired program code in the form of instructions or data structures and that can be accessed by a computer. A computer-readable medium may be tangible and non-transitory. As used herein, the term "code" may refer to software, instructions, code, or data that is/are executable by a computing device or a processor. A "module" denotes a processor configured to execute computer-readable code.

As described herein, a processor includes, but is not limited to, a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the herein described functions. A general purpose processor can be a microprocessor. Alternatively, the processor includes, but is not limited to, a controller, or microcontroller, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor includes, but is not limited to, primarily analog components. For example, any of the signal processing algorithms described herein may be implemented in analog circuitry. In some embodiments, a processor includes, but is not limited to, a graphics processing unit (GPU). The parallel processing capabilities of GPUs can reduce the amount of time for training and using neural networks (and other machine learning models) compared to central processing units (CPUs). In some embodiments, a processor includes, but is not limited to, an ASIC including dedicated machine learning circuitry custom-build for one or both of model training and model inference.

As described herein, tasks illustrated in the drawings can be distributed across multiple processors or computing devices of a computer system, including computing devices that are geographically distributed. The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims, and are also encompassed by the present disclosure.

In accordance with some embodiments of the present disclosure, a system and methods for labeling tractography in the presence of a brain lesion are provided. Some embodiments of the present disclosure involve combining a FWC tractography set and a non-FWC tractography set into a single tractography set with a "degree of free water" value assigned to at least one of a geometry of a neural tract (a neural tract geometry) and a geometry of a fragment of a neural tract (a neural tract fragment geometry). A tool, e.g., a graphical user interface, comprising a slider interface having a slider, is introduced to facilitate dynamically adjusting the free water threshold value that controls selecting and displaying tract geometry and/or a fragment of tract geometry. For example, only a geometry for each neural tract and a geometry for each fragment of a neural tract, corresponding to a degree of free water below a threshold value is displayed while other geometry is hidden.

In accordance with some embodiments of the present disclosure, by dynamically adjusting the degree of FWC applied, at least one of a neural tract geometry and a neural tract fragment geometry is selectively displayable, thereby eliminating any need to reprocess or regenerate a tract set. By assigning a normalized value, indicating a degree of free water, to at least one of a neural tract geometry and a neural tract fragment geometry and dynamically adjusting a free water threshold value, at least one of the neural tract geometry and the neural tract fragment geometry is selectively displayable for a plurality of distinct pathologies, thereby avoiding false positive results otherwise resulting from overcorrecting the free water threshold value in relation to certain non-pathological free water areas, e.g., the ventricles. Furthermore, a GUI, comprising a tool, such as a slider tool, is used to vary the free water threshold value. For example, by moving the slider tool to a setting of approximately 80%, only at least one of a neural tract geometry and a neural tract fragment geometry, having a free water value of up to approximately 80%, such as a geometry corresponding to a ventricle, is displayed.

Referring to FIG. 1, this block diagram illustrates functional subsystems of an MRI system 100, in accordance with an embodiment of the present disclosure. The MRI system 100 is shown for illustrative purposes only, and variations, including additional, fewer, and/or varied components are possible. MRI is an imaging modality that is primarily used to generate images from magnetic resonance (MR) signals, such as nuclear magnetic resonance (NMR) signals that emanate from hydrogen atoms, upon excitation, in an object. In medical MRI, typical signals of interest are NMR signals that emanate from the major hydrogen containing components, such as water and fat, of tissues, such as adipose tissue, upon excitation. The MRI system 100 comprises a data processing system 105. The data processing system 105 generally comprises one or more output devices, such as a display, one or more input devices, such as a keyboard and a mouse, as well as one or more processors coupled with a memory having volatile and persistent components. The data processing system 105 further comprises an interface, e.g., comprising an interface 200 (FIGS. 2 and 3), that is adapted for communication and data exchange with the hardware components of MRI system 100 that are used for performing a scan, e.g., an MRI scan.

Still referring to FIG. 1, the MRI system 100 further comprises a main field magnet 110. For example, the main field magnet 110 comprises at least one of a permanent magnet, a superconducting magnet, a resistive magnet, and a hybrid magnet. The main field magnet 110 is operable to produce a substantially uniform magnetic field B0 having a direction along an axis. The magnetic field B0 is used to create an imaging volume within which desired atomic nuclei, such as the protons in hydrogen atoms, e.g., within water and fat, of an object are magnetically aligned in preparation for a scan. In some implementations, as in this example implementation, the MRI system 100 further comprises a main field control unit 115 in communication with the data processing system 105, the data processing system 105 configured to control operation of the main field magnet 110.

Still referring to FIG. 1, the MRI system 100 further comprises gradient coils 120 configured to encode spatial information in the main magnetic field B0 along three perpendicular axis, for example. The size and configuration of the gradient coils 120 are such that they produce a controlled and uniform linear gradient. For example, three paired orthogonal current-carrying gradient coils 120 that are disposed within the main field magnet 110 are configured to produce desired linear gradient magnetic fields. The magnetic fields that are at least one of combinationally produced and sequentially by the gradient coils 120 are superimposed on the main magnetic field B0 such that selective spatial excitation of an object within the imaging volume occurs. In addition to allowing spatial excitation, the gradient coils 120 attach spatially specific frequency and phase information to the atomic nuclei, thereby facilitating reconstruction of the resultant MR signal into a useful image. The MRI system 100 further comprises a gradient coil control unit 125 in communication with the data processing system 105, the gradient coil control unit 125 configured to control the operation of the gradient coils 120.

Still referring to FIG. 1, the MRI system 100 further comprises radio frequency (RF) coils 130. The RF coils 130 are configured to establish a magnetic field B1 for exciting the atomic nuclei or "spins." The RF coils 130 are further configured to detect signals emitted from the "relaxing" spins within the object being imaged. Accordingly, the RF coils 130 comprise at least one of separate transmit-coils and receive-coils and a combined transmit-coil and receive-coil having a switching mechanism for switching between a transmit mode and a receive mode.

Still referring to FIG. 1, the RF coils 130 further comprise surface coils, which are typically receive only coils and/or volume coils which can receive and transmit coils. RF coils 130 can be integrated in the main field magnet 110 bore. Alternatively, RF coils 130 can be implemented proximate the object to be scanned, such as a head, and the RF coils 130 can be configured in a shape that approximates the shape of the object, such as a close-fitting helmet. The MRI system 100 further comprises an RF coil control unit 135 in communication with the data processing system 105, the RF coil control unit 135 is configured to control the operation of the RF coils 130.

Still referring to FIG. 1, to generate an image, the MRI system 100 detects a presence of atomic nuclei containing spin angular momentum in an object, such as those of hydrogen protons in water or fat found in tissues, by subjecting the object to a large magnetic field. In this example implementation, the main magnetic field is denoted as B0; and the atomic nuclei, having a spin angular momentum, comprise protons, e.g., hydrogen protons. The magnetic field B0 partially polarizes the hydrogen protons in the object placed in the imaging volume of the main magnet 110. The protons are then excited with appropriately tuned RF radiation, e.g., the magnetic field B1, in this example. Finally, a weak RF radiation signal, emanating from the excited protons, is detected as protons "relax" from the magnetic interaction. The frequency of the detected signal is proportional to the magnetic field to which the protons are subjected. A cross-section of the object from which to obtain signals is selected by producing a magnetic field gradient across the object so that magnetic field values of B0 can be varied along a plurality of locations in the object. Given that the signal frequency is proportional to the varied magnetic field that is generated, the variations in magnetic field allow assigning a particular signal frequency and a particular phase to a location in the object. Accordingly, sufficient information is provided by the acquired signals to generate a map of the object in terms of proton presence, such map being the basis of an MRI image. For example, since proton density varies with the type of tissue, tissue variations can be mapped as image contrast variations after the obtained signals are processed.

Still referring to FIG. 1, to obtain images from the MRI system 100 in the manner described above, one or more sets of RF pulses and gradient waveforms (collectively called "pulse sequences") are selected at the data processing system 105. The data processing system 105 passes the selected pulse sequence information to the RF control unit 135 and the gradient control unit 125, which collectively generate the associated waveforms and timings for providing a sequence of pulses to perform a scan.

Still referring to FIG. 1, for tractography, the data processing system 105 uses diffusion tensor imaging (DTI) techniques to map white matter tractography in the brain by: measuring the apparent diffusion coefficient at each voxel in the image, and, after multilinear regression across multiple images, reconstructing the whole diffusion tensor, thereby providing MRI images with each anisotropy linked to an orientation of the predominant axis (predominant direction of the diffusion). Post-processing programs are used to extract this directional information, and, by introducing a color code, indicate a manner wherein the fibers are oriented in a 3D coordinate system (known as an "anisotropic map") where, for example, red indicates directions in the X axis: right to left or left to right, green indicates directions in the Y axis: posterior to anterior or from anterior to posterior, and blue indicates directions in the Z axis: foot-to-head direction or vice versa.

Figure 2:
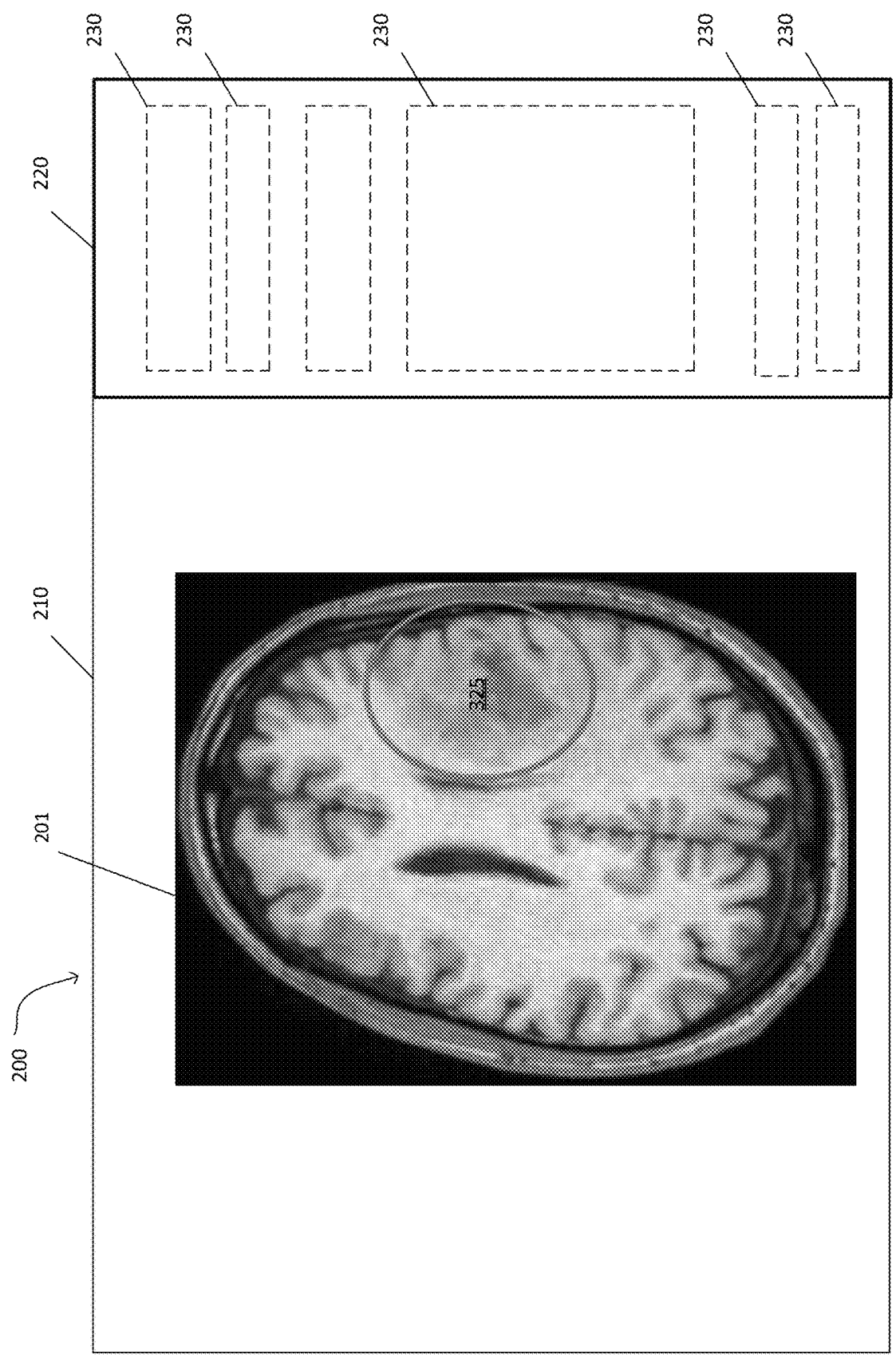
FIG. 2 is a diagram illustrating an MRI graphical user interface for tractography having a free water correction (FWC) slider interface.

Referring to FIG. 2, this diagram illustrates an MRI graphical user interface 200 for tractography, in accordance with an embodiment of the present disclosure. The MRI graphical user interface 200 comprises: a first area 210 for displaying an image 201 acquired, for example, by using the MRI system 100, as shown in FIG. 1; and a second area 220 having user interface elements 230 for controlling aspects of the image 201 displayed in the first area 210, such as selectable features, e.g., such checkboxes (not shown), to select an option, e.g., "intersecting tracts only," or for filtering data, such as hiding certain fibers, e.g., blue marked motor fibers that run from head-to-foot, red marked fibers running from left-to-right for carrying information to different hemispheres of the brain, or green marked projection fibers connecting lower order processing regions and higher order processing regions of the brain. The user interface elements 230 comprise an FWC slider 330 (FIG. 3).

Figure 3:
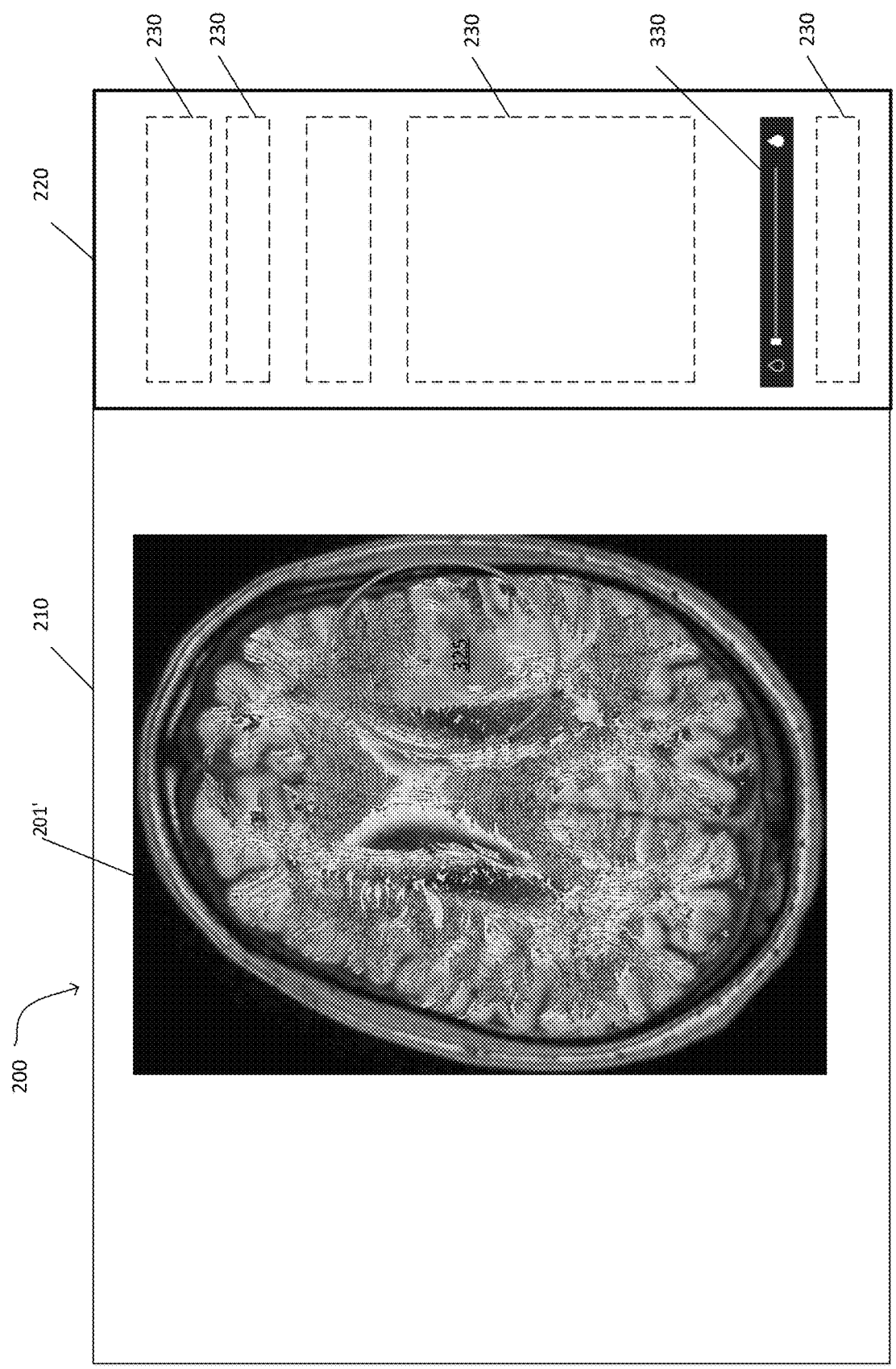
FIG. 3 is a diagram illustrating the MRI graphical user interface, as shown in FIG. 1, with the FWC slider interface user interface set at a free water value of 0%.

Referring to FIG. 3, this diagram illustrates the MRI graphical user interface 200, as shown in FIG. 2, wherein the FWC slider 330 is set at a free water value of 0%, in accordance with an embodiment of the present disclosure. The image 201, as shown in FIG. 2, is enhanced, thereby displaying a refreshed image 201' which includes a tractography set showing bundles of tracts, wherein an area 325 denotes an area of increased free water due, for example, to an edema. As discussed above, whereas tractography algorithms can identify approximately 90% of nerve tracts, such tractography algorithms can be confounded by areas of increased free water, such as area 325, which hide anisotropic water, e.g., tracts, during MRI. Therefore, according to an embodiment of the present disclosure, the second area 220 of the user interface elements 230 comprises an FWC slider 330 to facilitate at least one of controlling and selecting at least one of a tract geometry and tract fragment geometry to be displayed based on a degree of free water in the image 201 by using a method M4, as shown in FIG. 4, by example only, whereby the refreshed image 201' is displayable.

Figure 4:
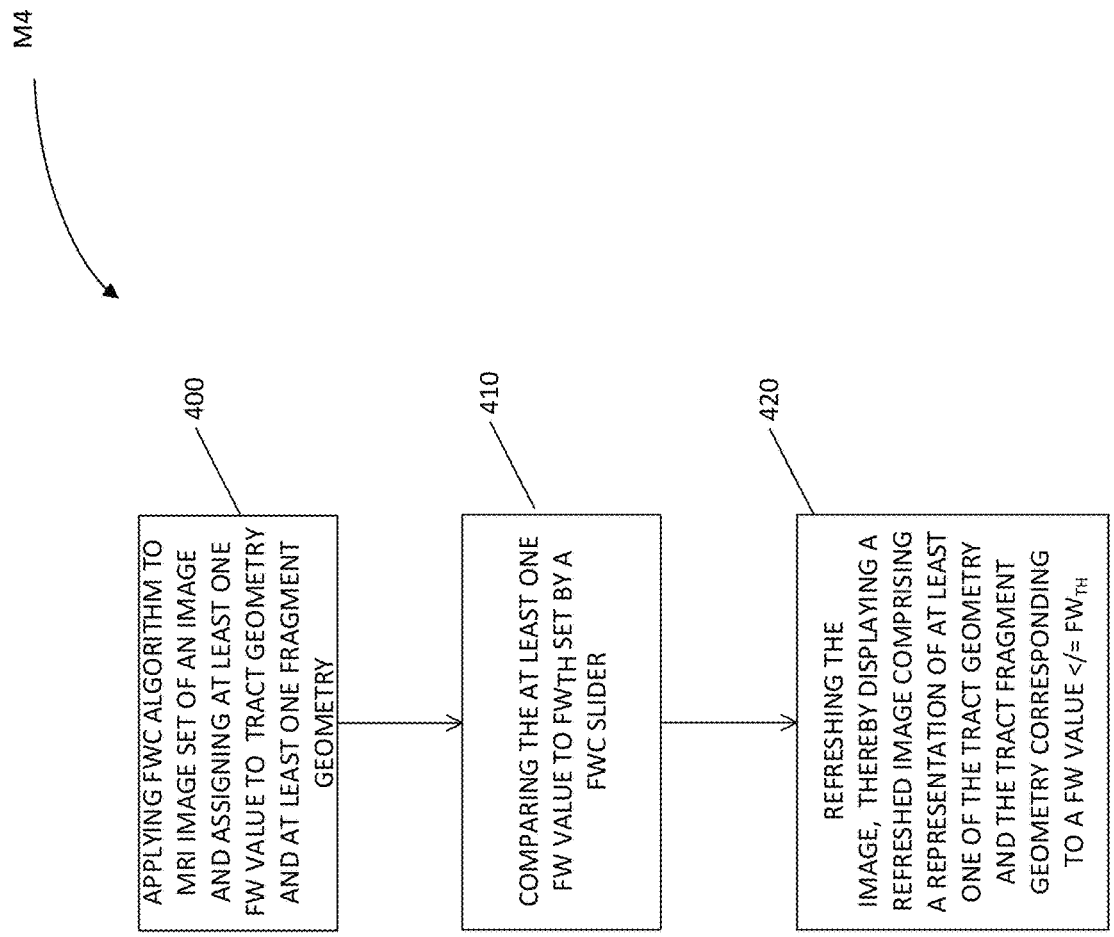
FIG. 4 is a flow diagram illustrating a method of controlling and selecting at least one of a tract geometry and tract fragment geometry to be displayed, based on a degree of free water in an image, e.g., the image, as shown in FIG. 2, by way of an MRI graphical user interface, as shown in FIG. 1, wherein an FWC slider, as shown in FIG. 3, is set at a free water value of 0%.

Referring to FIG. 4, this flow diagram illustrates a method M4 of controlling and selecting at least one of a tract geometry and a tract fragment geometry to be displayed, based on a degree of free water in an image, e.g., the image 201, as shown in FIG. 2, by way of an MRI graphical user interface, as shown in FIG. 1, wherein an FWC slider 330, as shown in FIG. 3, is set at a free water value of 0%, in accordance with an embodiment of the present disclosure. The method M4 comprises: applying an FWC algorithm to an MRI image set and assigning at least one FW value to at least one of a tract geometry and tract fragment geometry, as indicated by block 400; comparing the at least one FW value to a threshold ($FW_{TH}$), e.g., as user-selected, as set via an FWC slider 330, as indicated by block 410; and refreshing the image 201, thereby displaying a refreshed image 201' comprising a representation of at least one of the tract geometry and the tract fragment geometry corresponding to a FW value$</=FW_{TH}$, as indicated by block 420.

Still referring to FIG. 4, at block 400, an FWC algorithm is applied to the MRI image set resulting in a tractography set with a "degree of free water" value (FW value) assigned to each tract and/or fragment of tract geometry. As discussed above, the FWC algorithm comprises any of a number of algorithms, such as described in Henderson, et al. At block 410, the FW values assigned to all tracts and/or and fragments of tract geometry are compared with a user selected threshold ($FW_{TH}$) indicated by the FWC slider 330. At block 420, the image 201 is refreshed as a refreshed image 201' so that only those tracts and/or fragments of tract geometry having FW values$</=FW_{TH}$ in the area 325 are displayed, while others are hidden. If the FWC slider 330 is set to 0%, as shown in FIG. 3, such that the refreshed image 201' shows only tracts/segments where the FW value$</=FW_{TH}=0$, no free water correction is applied. Thus, the area 325 of the image 201 has gaps in tractography due to signal washout from increased free water.

Figure 5:
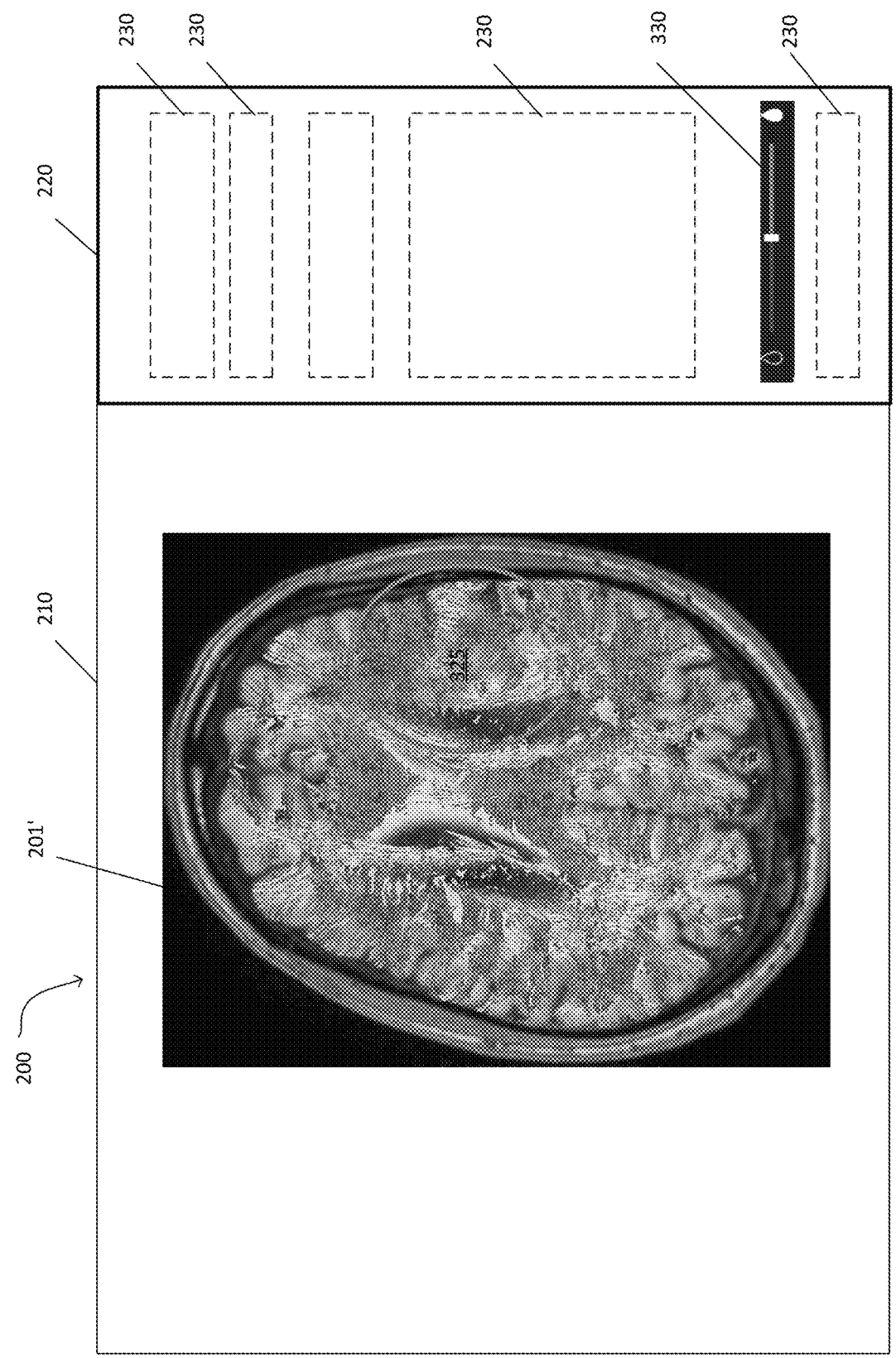
FIG. 5 is a diagram illustrating the MRI graphical user interface, as shown in FIG. 1, with the FWC slider interface user interface set at a free water value of 50%.

Referring to FIG. 5, this diagram illustrates the MRI graphical user interface 200, as shown in FIG. 1, wherein the FWC slider 330 is set at a free water value of 50%, such that the refreshed image 201' shows additional tracts that are "barely" hidden by free water, e.g., tracts where the assigned the FW values$<FW_{TH}=50\%$, in the area 325, in accordance with an embodiment of the present disclosure. Setting the slider 330 at 50% may or may not actually map to a 50% free water value, since, in embodiments, the slider value may be remapped via a look-up table to ensure uniform-visibility control over the entire range of the slider 330, thereby avoiding problems otherwise arising when a large portion of the FW values fall into a very narrow range such that an incremental movement of the slider would hide too many tracts/segments/points at one position on the slider, and otherwise removing too little (or none) of the tracts/segments/points at another position on the slider 330.

Figure 6:
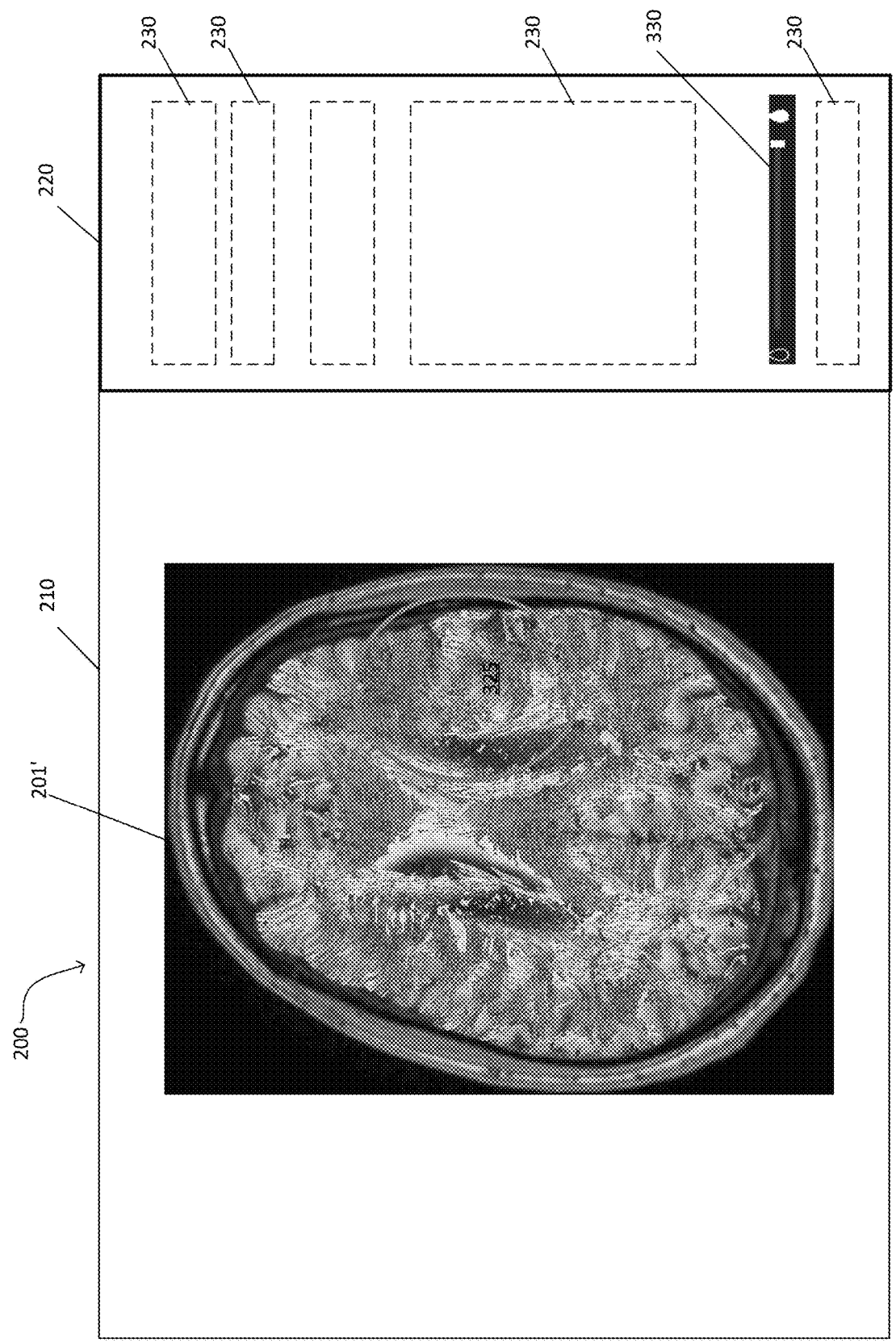
FIG. 6 is a diagram illustrating the MRI graphical user interface, as shown in FIG. 1, with the FWC slider interface user interface set at a free water value of 100%.

Referring to FIG. 6, this diagram illustrates the MRI graphical user interface of FIG. 1 wherein the FWC slider 330 is set at a free water value of 100% for effecting an aggressive free water correction, such that the refreshed image 201' shows all tracts, wherein the assigned FW values<FWTH=100%, e.g., full free water corrected tractography, including tracts that were significantly occluded by free water, in the area 325, in accordance with an embodiment of the present disclosure.

Figure 7:
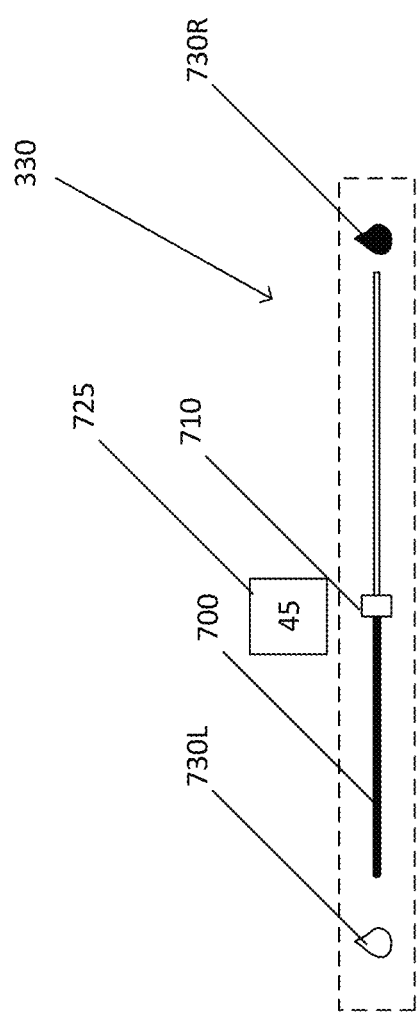
FIG. 7 is a diagram illustrating additional details of the FWC slider interface user interface.

Referring to FIG. 7, this diagram illustrates additional details of the FWC slider interface user interface, comprising the slider interface 330, as shown in FIGS. 3, 5, and 6, in accordance with an embodiment of the present disclosure. The slider interface 330 comprises a track 700 for facilitating setting a range by a user. From left-to-right, the smallest threshold value appears on the far left end of the track 700 and the largest value is on the far right. The slider interface 330 further comprises a position indicator 710, e.g. a "thumb" feature, configured to slide along the track 700. Optionally, the slider interface 330 further comprises a value label 725 disposed in relation to the position indicator 710, the value label 725 configured to display the value of its position as a numeral, e.g., "45" for $FW_{TH}=45\%$. As a further option, the slider interface 330 further comprises tick marks (not shown) disposed along the track 700, the tick marks representing predetermined values, e.g., 0%. 10%, 20%, . . . , 100%, to which the user can set by moving the position indicator 710. The slider interface 330 further comprises icons 730L and 730R disposed at respective ends of the track 700 to provide a visual representation of a range of threshold values, the icon 730L indicating no free water correction, and the icon 730R indicating full free water correction.

Still referring to FIG. 7, for example, whereas the exemplary FWC slider 330 shows the smallest threshold value appearing on the far left end of the track 700 and the largest value on the far right, the FWC slider 330 can be implemented in the opposite direction, from right-to-left, wherein the left position shows the full water corrected set and right position shows the uncorrected set. The system should therefore not be limited by the above described embodiment, method, and examples, but by all embodiments and methods within the scope and spirit of the system. Thus, the present disclosure is not intended to be limited to the implementations shown herein but is to be accorded the widest scope consistent with the principles and novel features herein disclosed.

Some embodiments of the present disclosure also encompass MRI systems and methods for labeling tractography in a presence of a brain lesion. While accounting for tractography infiltration or displacement, these embodiments of the MRI systems and methods involve providing an initial estimation of at least one of: (a) an infiltration or an infiltrative and (b) a displacement or a displacing effect; and providing a tool to the user to adjust the level of at least one of: (a) an infiltration or an infiltrative and (b) a displacement or a displacing effect to intraoperatively re-perform the tract segmentation in at least near real-time. For example, the tool comprises a graphical user interface (GUI) slider tool for use in surgical planning software.

These embodiments of the MRI systems and methods further involve modeling a force that is exerted by a lesion on the brain by virtually locally deforming a tract labeling atlas in a 3D space by way of the tool. By example only, the tool comprises a slider. Modeling this force comprises using at least one of a size, a shape, and a level of displacement, as defined by the tool, e.g., the slider, wherein using the slider to increase a level of displacement virtually increases the force. In the case of purely infiltrative disease, e.g., no displacement, no force would be modeled; and an atlas would not be deformed. Further, the MRI systems and methods would instruct the labeling feature to expect fewer tracts in that area and to label tracts, accordingly, including labeling tracts in an area corresponding to a pathology, itself.

Figure 8:
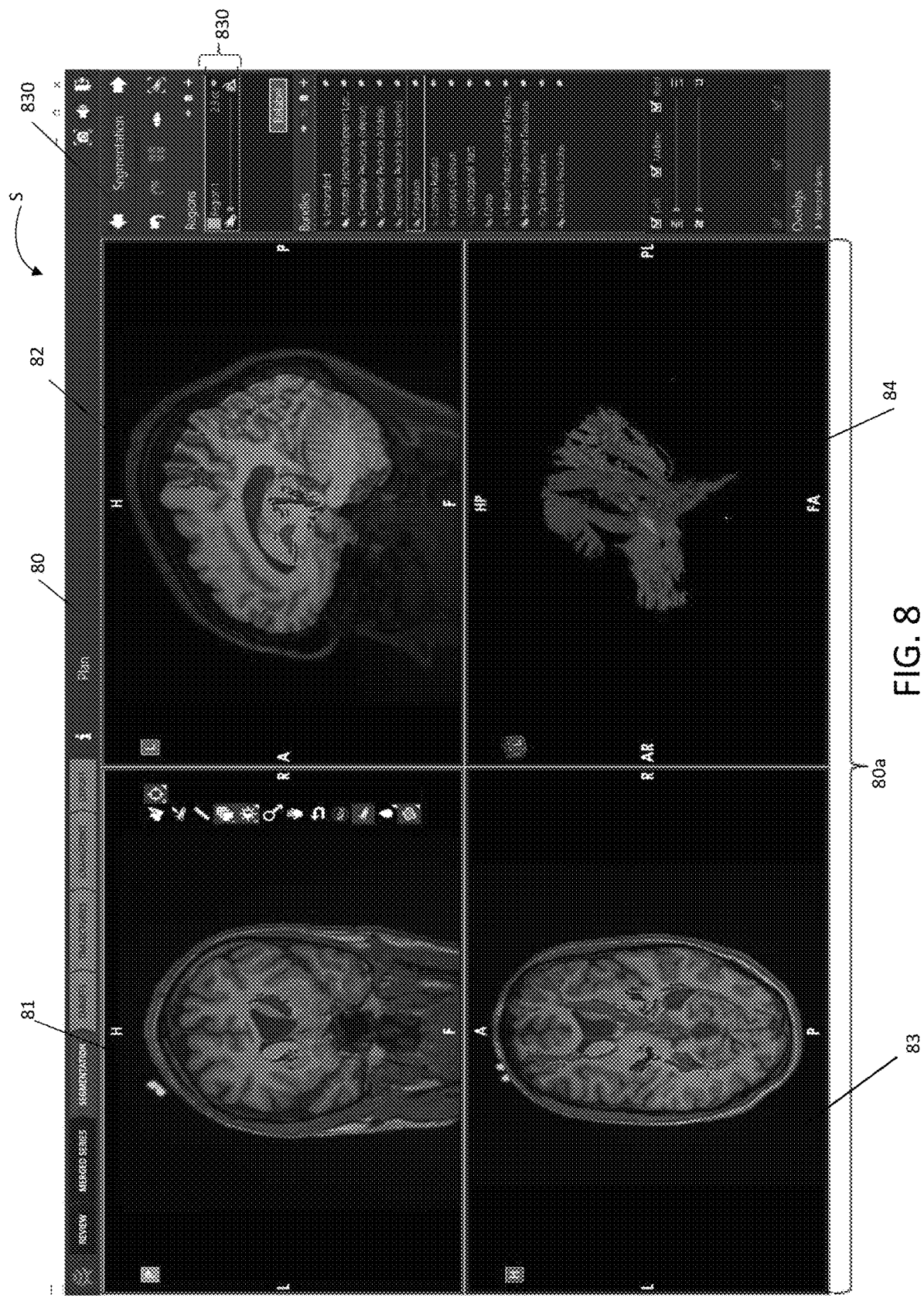
FIG. 8 is a screenshot illustrating an MRI user interface system for labeling tractography from surgical planning data in a presence of a lesion in a brain, the tractography comprising a tract segmentation and a tract labeling atlas in relation to a three-dimensional space.

Referring to FIG. 8, this screenshot illustrates an MRI user interface system S comprising a UI 80 configured for use with an MRI system, the UI 80 comprising a slider feature 820, the slider feature 820 configured to facilitate modeling a force exerted by a lesion on a brain by virtually locally deforming a tract labeling atlas in a 3D space per-region by way of the tool, e.g., a slider 830, in accordance with an embodiment of the present disclosure. By example only, the UI 80 comprises a display 80a of an object or a subject, such as a patient, respectively showing a cross-sectional views 81, 82, 83, along three axes, e.g., a front to rear axis, a side to side axis and a top to bottom axis.

Figure 9:
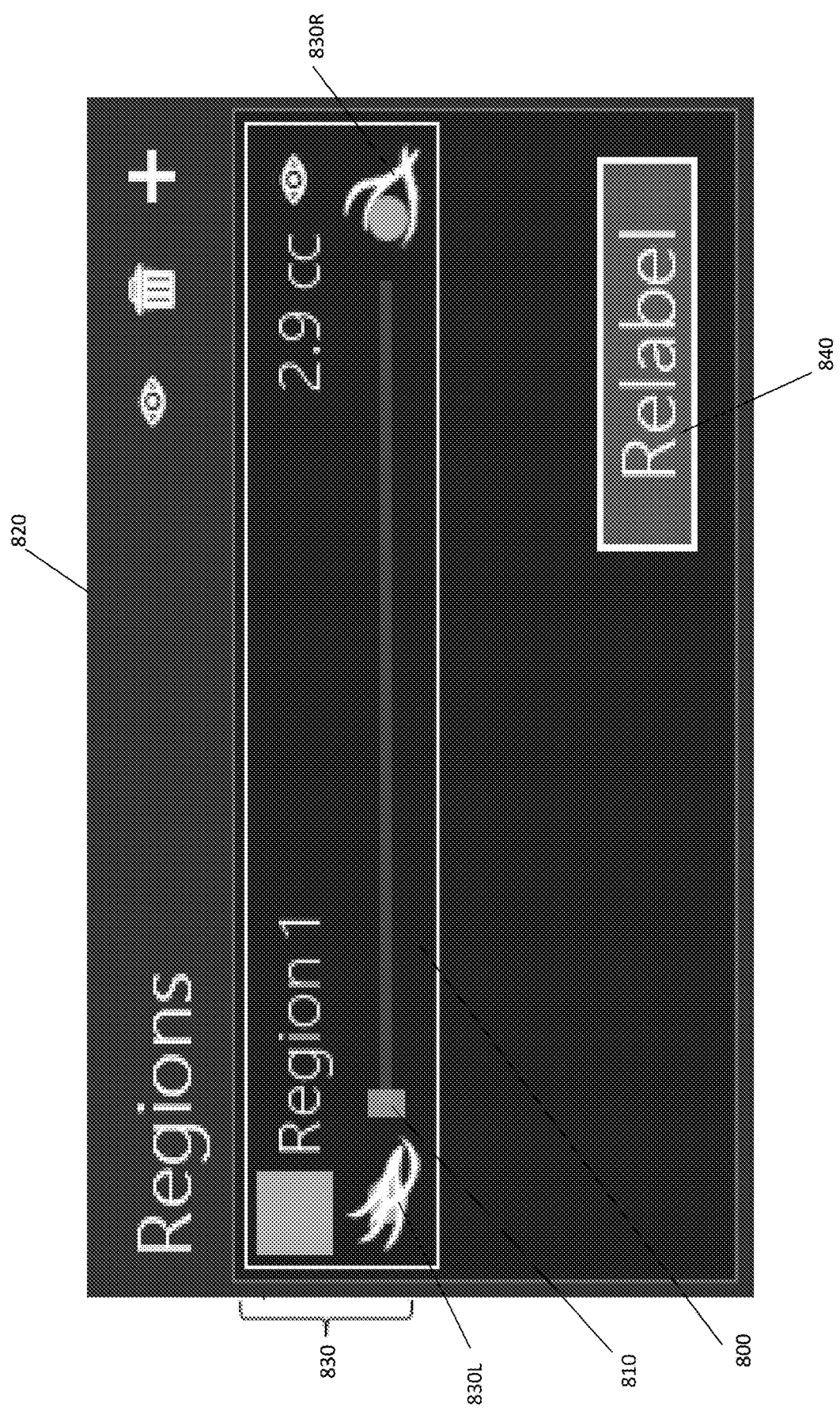
FIG. 9 is a screenshot illustrating a slider feature of a UI, as shown in FIG. 8.

Referring to FIG. 9, this screenshot illustrates a slider feature 820 of a UI 80, as shown in FIG. 8, in accordance with an embodiment of the present disclosure. The slider feature 820 comprises a slider interface 830. The slider interface 830 comprises a track 800 for facilitating setting at least one of a size, a shape, and a level of displacement by a user. From left-to-right, the smallest threshold value appears on the far left end of the track 800 and the largest value is on the far right. The slider interface 830 further comprises a position indicator 810, e.g. a "thumb" feature, configured to slide along the track 800. Optionally, the slider interface 830 further comprises a value label (not shown) disposed in relation to the position indicator 810, the value label configured to display the value of its position as a numeral, e.g., with units. As a further option, the slider interface 830 further comprises tick marks (not shown) disposed along the track 800, the tick marks representing predetermined values to which the user can set by moving the position indicator 810. The slider interface 830 further comprises icons 830L and 830R disposed at respective ends of the track 800 to provide a visual representation of a range of threshold values, the icon 830L indicating presence of a fully infiltrative disease condition, and, thus, no displacement, no force modeled, and no atlas deformation, and the icon 830R indicating full mass effect, and, thus, displacement, a force modeled; and atlas deformation. The slider feature 820 further comprises a button 840 for triggering relabeling of the tractography.

Figure 10:
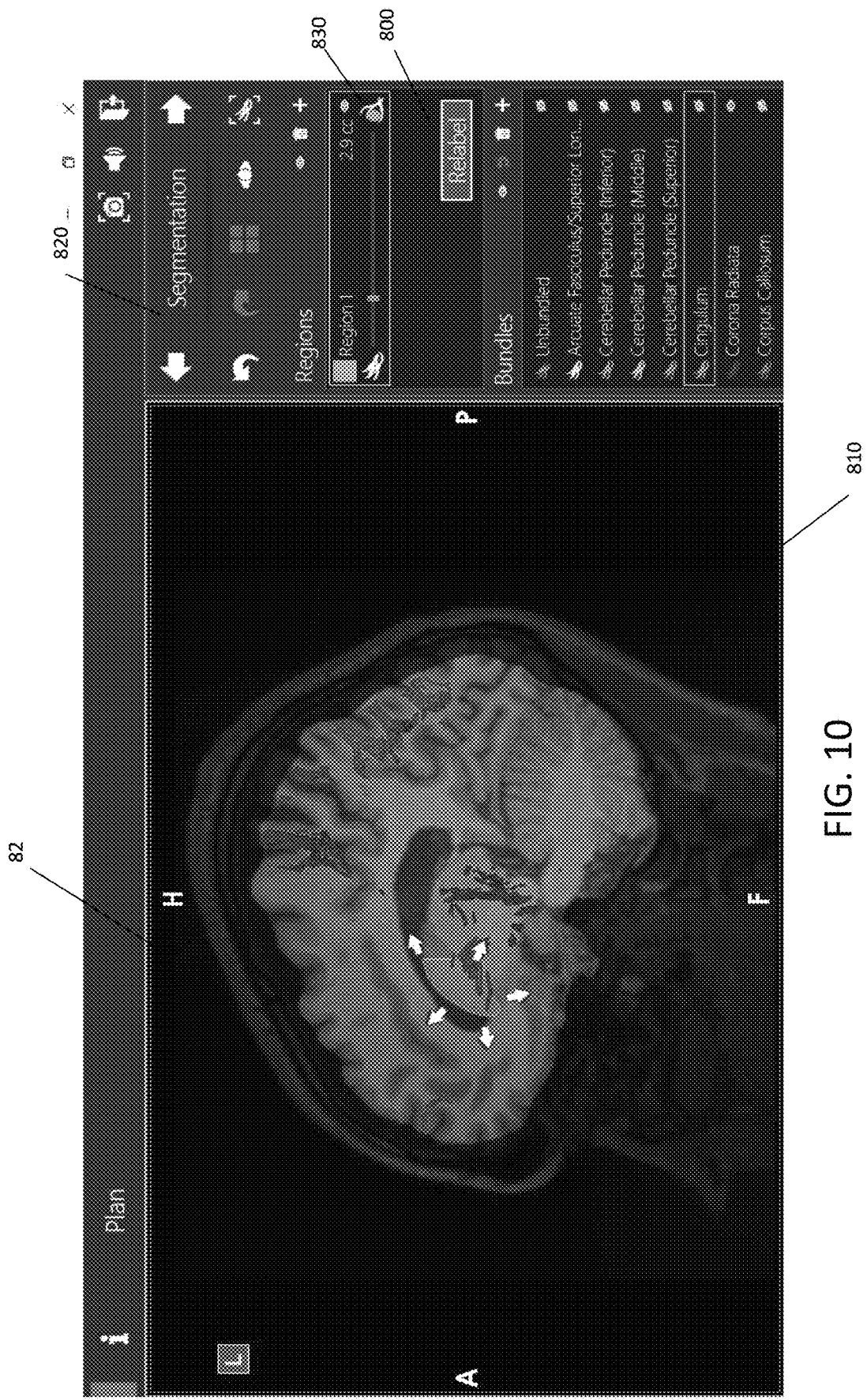
FIG. 10 is a screenshot illustrating a cross-sectional view, along the side to side axis, of the display in the UI, as shown in FIG. 8, wherein the position indicator has been slid along the track, as shown in FIG. 9.

Referring to FIG. 10, this screenshot illustrates a cross-sectional view 82, along the side to side axis, of the display 80a in the UI 80, as shown in FIG. 8, wherein the position indicator 810, e.g. a "thumb" feature, has been slid along the track 800, as shown in FIG. 9, in accordance with an embodiment of the present disclosure. When the position indicator 810 is slid to the right, the region is now identified as introducing mild mass effect. At this point, clicking button 840 having the indicium "Relabel" triggers re-performance of the segmentation, wherein a "force vector" field corresponds to a pathology region, and wherein the atlas is locally distorted based on the force vector field.

Figure 11:
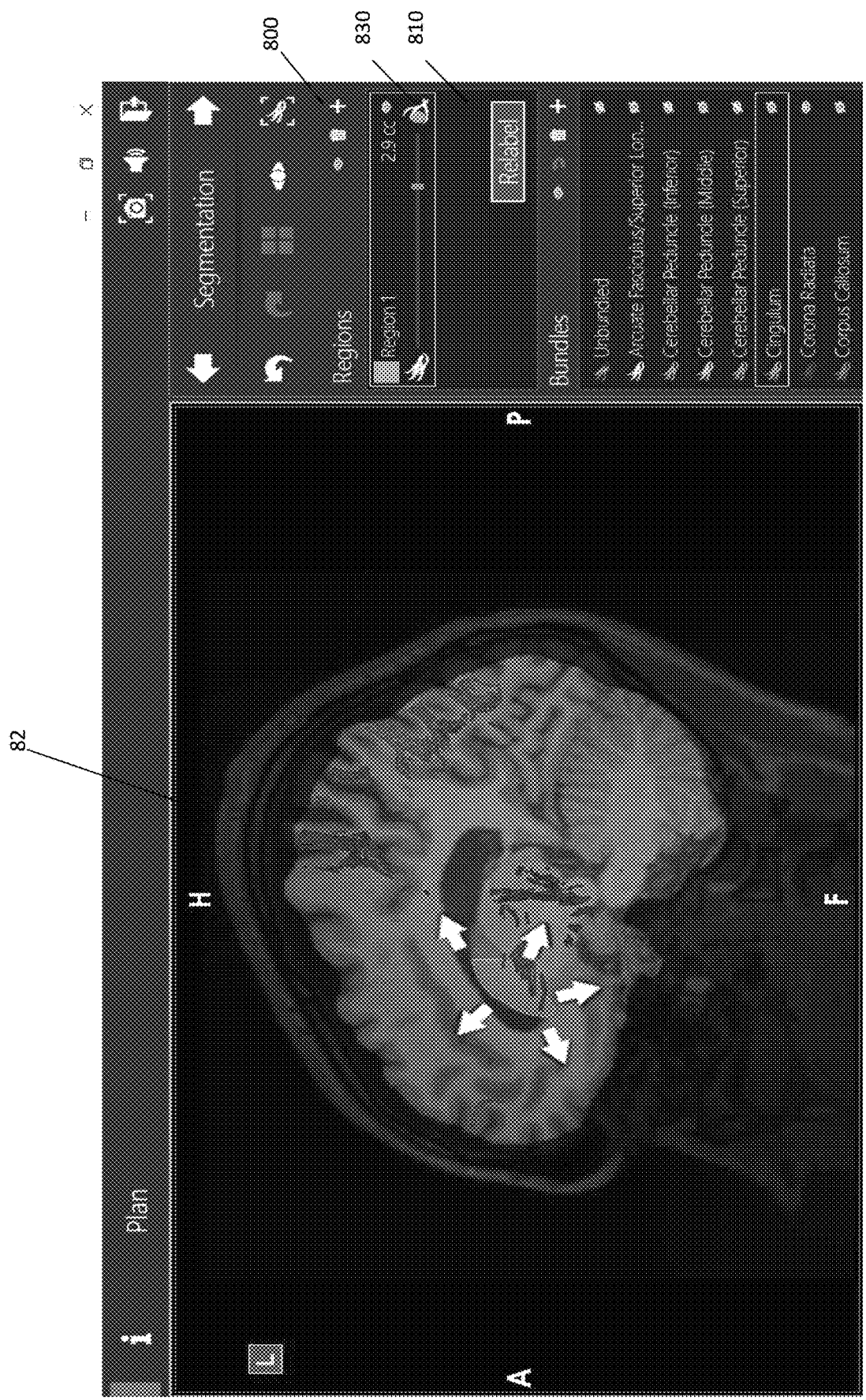
FIG. 11 is a screenshot illustrating a cross-sectional view, along the side to side axis, of the display in the UI, as shown in FIG. 8, wherein the position indicator, has been slid farther along the track, as shown in FIG. 9.

Referring to FIG. 11, this screenshot illustrates a cross-sectional view 82, along the side to side axis, of the display 80a in the UI 80, as shown in FIG. 8, wherein the position indicator 810, e.g. a "thumb" feature, has been slid farther along the track 800, as shown in FIG. 9, in accordance with an embodiment of the present disclosure. When the position indicator 810 is slid farther to the right, the region is now identified as introducing stronger mass effect than that shown in FIG. 10. At this point, clicking button 840 having the indicium "Relabel" triggers re-performance of the segmentation, wherein a new "force vector" field corresponds to a pathology region, and wherein the atlas is locally distorted based on the new force vector field, e.g., a stronger "force vector" field than that shown in FIG. 10.

Figure 12:
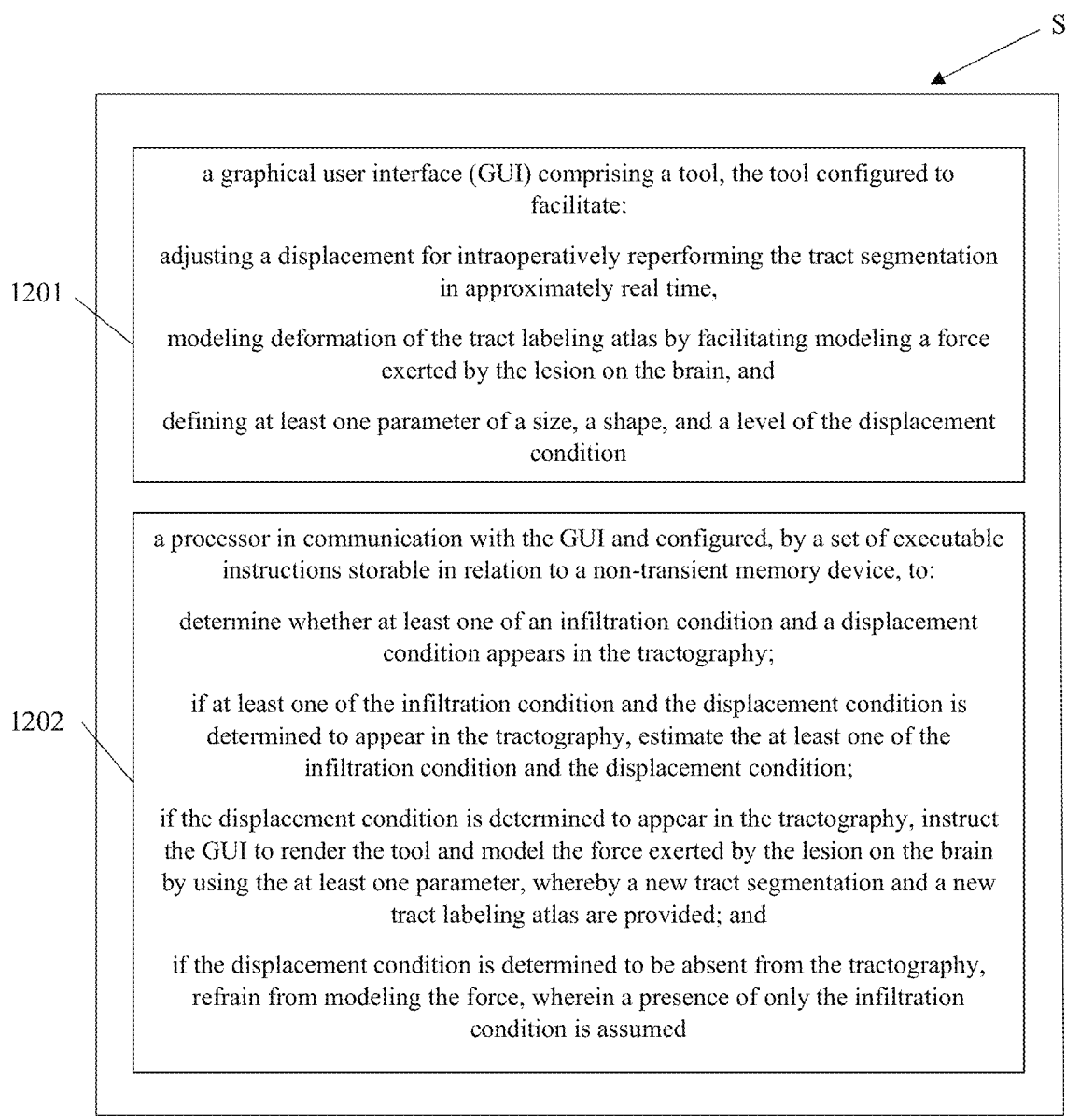
FIG. 12 is a flow diagram illustrating an MRI user interface system for labeling tractography from surgical planning data in a presence of a lesion in a brain, the tractography comprising a tract segmentation and a tract labeling atlas in relation to a three-dimensional space.

Referring back to FIG. 12, an MRI user interface system S for labeling tractography from surgical planning data in a presence of a lesion in a brain, the tractography comprising a tract segmentation and a tract labeling atlas in relation to a three-dimensional space, the system comprising: a GUI 1201, e.g., the UI 80, comprising a tool, e.g., a slider feature 820 comprising a slider interface 830, the tool configured to facilitate: adjusting a displacement for intraoperatively reperforming the tract segmentation in approximately real time, modeling deformation of the tract labeling atlas by facilitating modeling a force exerted by the lesion on the brain, and defining at least one parameter of a size, a shape, and a level of the displacement condition; and a processor 1202 in communication with the GUI and configured, by a set of executable instructions storable in relation to a non-transient memory device, to: determine whether at least one of an infiltration condition and a displacement condition appears in the tractography; if at least one of the infiltration condition and the displacement condition is determined to appear in the tractography, estimate the at least one of the infiltration condition and the displacement condition; if the displacement condition is determined to appear in the tractography, instruct the GUI to render the tool and model the force exerted by the lesion on the brain by using the at least one parameter, whereby a new tract segmentation and a new tract labeling atlas are provided; and if the displacement condition is determined to be absent from the tractography, refrain from modeling the force, wherein a presence of only the infiltration condition is assumed, in accordance with an embodiment of the present disclosure.

Still referring back to FIG. 12, in the system S, the tool comprises a slider feature, e.g., a slider feature 820; and the slider feature comprises a slider. the GUI is configured to render a display of at least one of an object and a subject, the display showing at least one cross-sectional view, the at least one cross-sectional view comprising at least one view along at least one of three axes, and the three axes comprising a front to rear axis, a side to side axis, and a top to bottom axis. The slider feature, e.g., a slider feature 820, comprises at least one of: a slider interface, e.g., a slider interface 830; a track, e.g., a track 800, for facilitating setting at least one of a size, a shape, and a level of displacement by a user, a representation, e.g., an icon 830L, of the lowest threshold value is disposed on a far left end of the track, and a representation of the highest value, e.g., an icon 830R, is disposed on a far right end of the track; and a position indicator, e.g., a position indicator 810, configured to slide along the track, the position indicator comprising a thumb feature.

Still referring back to FIG. 12, in the system S, the slider interface, e.g., a slider interface 830, further comprises at least one of: a value label disposed in relation to the position indicator, e.g., a position indicator 810, the value label configured to display at least one of a value corresponding to a position of the position indicator, e.g., a position indicator 810, the value represented as a numeral; a plurality of tick marks disposed along the track, e.g., a track 800, the tick marks representing a plurality of predetermined values to which the position indicator, e.g., a position indicator 810, is movable; and a plurality of icons, the plurality of icons comprising a left end icon, e.g., an icon 830L, and a right end icon, e.g., an icon 830R, disposed at respective ends of the track, e.g., a track 800, to provide a visual representation of a range of threshold values, the left end icon, e.g., an icon 830L, indicating presence of a fully infiltrative disease condition, and, thus, no displacement, no force modeled, and no atlas deformation, and the right end icon, e.g., an icon 830L, indicating full mass effect, and, thus, displacement, a force modeled; and atlas deformation; and a button configured for trigger relabeling of the tractography.

Figure 13:
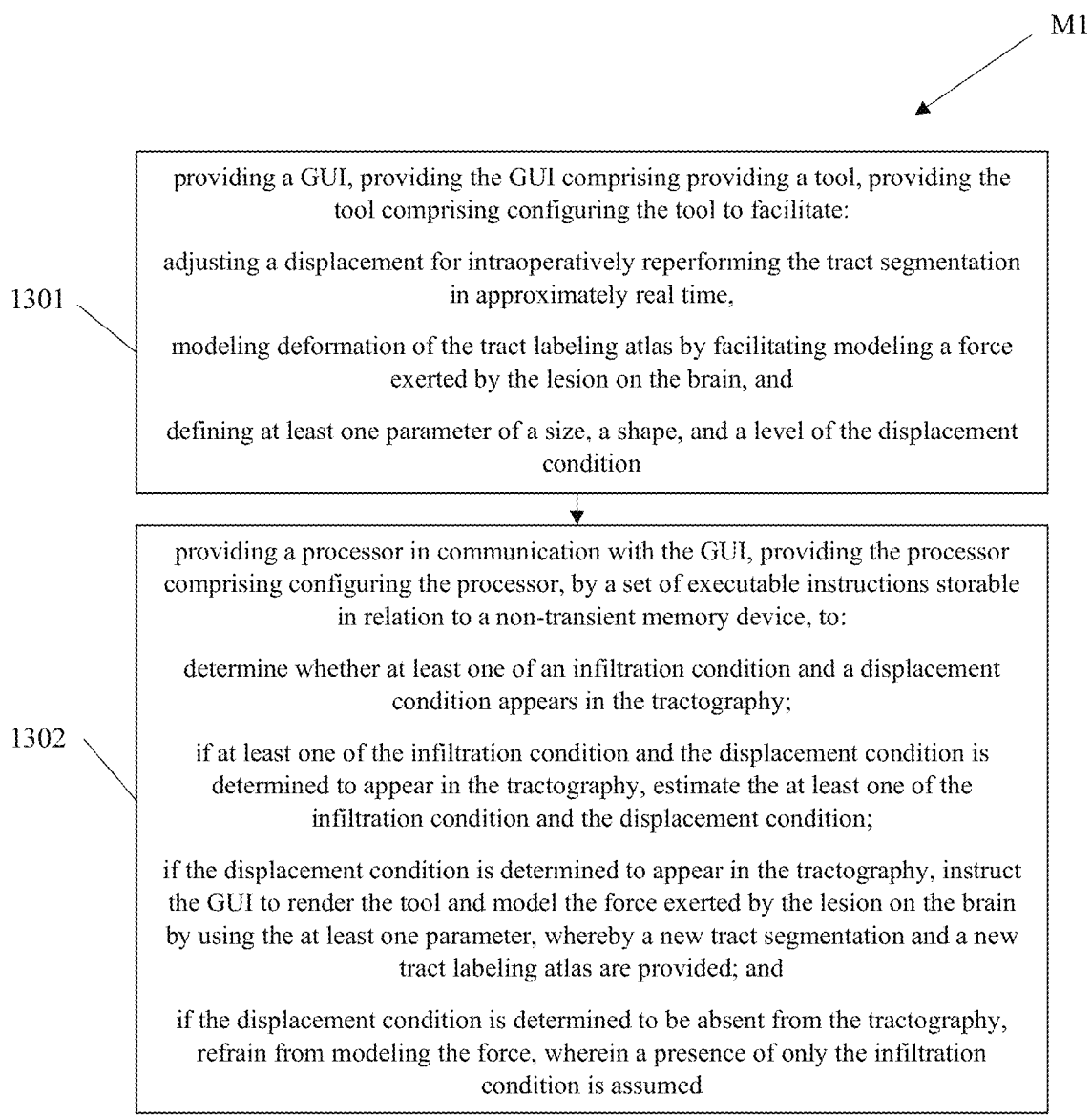
FIG. 13 is a flow diagram illustrating a method of providing an MRI user interface system for labeling tractography from surgical planning data in a presence of a lesion in a brain, the tractography comprising a tract segmentation and a tract labeling atlas in relation to a three-dimensional space.

Referring to FIG. 13, this flow diagram illustrates a method M1 of providing an MRI user interface system S for labeling tractography from surgical planning data in a presence of a lesion in a brain, the tractography comprising a tract segmentation and a tract labeling atlas in relation to a three-dimensional space, in accordance with an embodiment of the present disclosure. The method M1 comprises: providing a GUI 1201, e.g., the UI 80, providing the GUI comprising providing a tool, e.g., a slider feature 820 comprising a slider interface 830, providing the tool comprising configuring the tool to facilitate: adjusting a displacement for intraoperatively reperforming the tract segmentation in approximately real time, modeling deformation of the tract labeling atlas by facilitating modeling a force exerted by the lesion on the brain, and defining at least one parameter of a size, a shape, and a level of the displacement condition, as indicated by block 1301; and providing a processor in communication with the GUI, providing the processor comprising configuring the processor, by a set of executable instructions storable in relation to a non-transient memory device, to: determine whether at least one of an infiltration condition and a displacement condition appears in the tractography; if at least one of the infiltration condition and the displacement condition is determined to appear in the tractography, estimate the at least one of the infiltration condition and the displacement condition; if the displacement condition is determined to appear in the tractography, instruct the GUI to render the tool and model the force exerted by the lesion on the brain by using the at least one parameter, whereby a new tract segmentation and a new tract labeling atlas are provided; and if the displacement condition is determined to be absent from the tractography, refrain from modeling the force, wherein a presence of only the infiltration condition is assumed, as indicated by block 1302.

Still referring to FIG. 13, in the method M1, providing the tool comprises providing a slider feature; and providing the slider feature comprises providing a slider. Providing the GUI comprises configuring the GUI to render a display of at least one of an object and a subject, the display showing at least one cross-sectional view, the at least one cross-sectional view comprising at least one view along at least one of three axes, and the three axes comprising a front to rear axis, a side to side axis, and a top to bottom axis. Providing the slider feature comprises providing a slider interface. Providing the slider interface comprises: providing a track for facilitating setting at least one of a size, a shape, and a level of displacement by a user, a representation of the lowest threshold value is disposed on a far left end of the track, and a representation of the highest value is disposed on a far right end of the track; and providing a position indicator configured to slide along the track, the position indicator comprising a thumb feature.

Still referring to FIG. 13, in the method M1, providing the slider interface further comprises providing at least one of: a value label disposed in relation to the position indicator, the value label configured to display at least one of a value corresponding to a position of the position indicator, the value represented as a numeral; a plurality of tick marks disposed along the track, the tick marks representing a plurality of predetermined values to which the position indicator movable; and a plurality of icons, the plurality of icons comprising a left end icon and a right end icon disposed at respective ends of the track to provide a visual representation of a range of threshold values, the left end icon indicating presence of a fully infiltrative disease condition, and, thus, no displacement, no force modeled, and no atlas deformation, and the right end icon indicating full mass effect, and, thus, displacement, a force modeled; and atlas deformation; and a button configured for trigger relabeling of the tractography.

Figure 14:
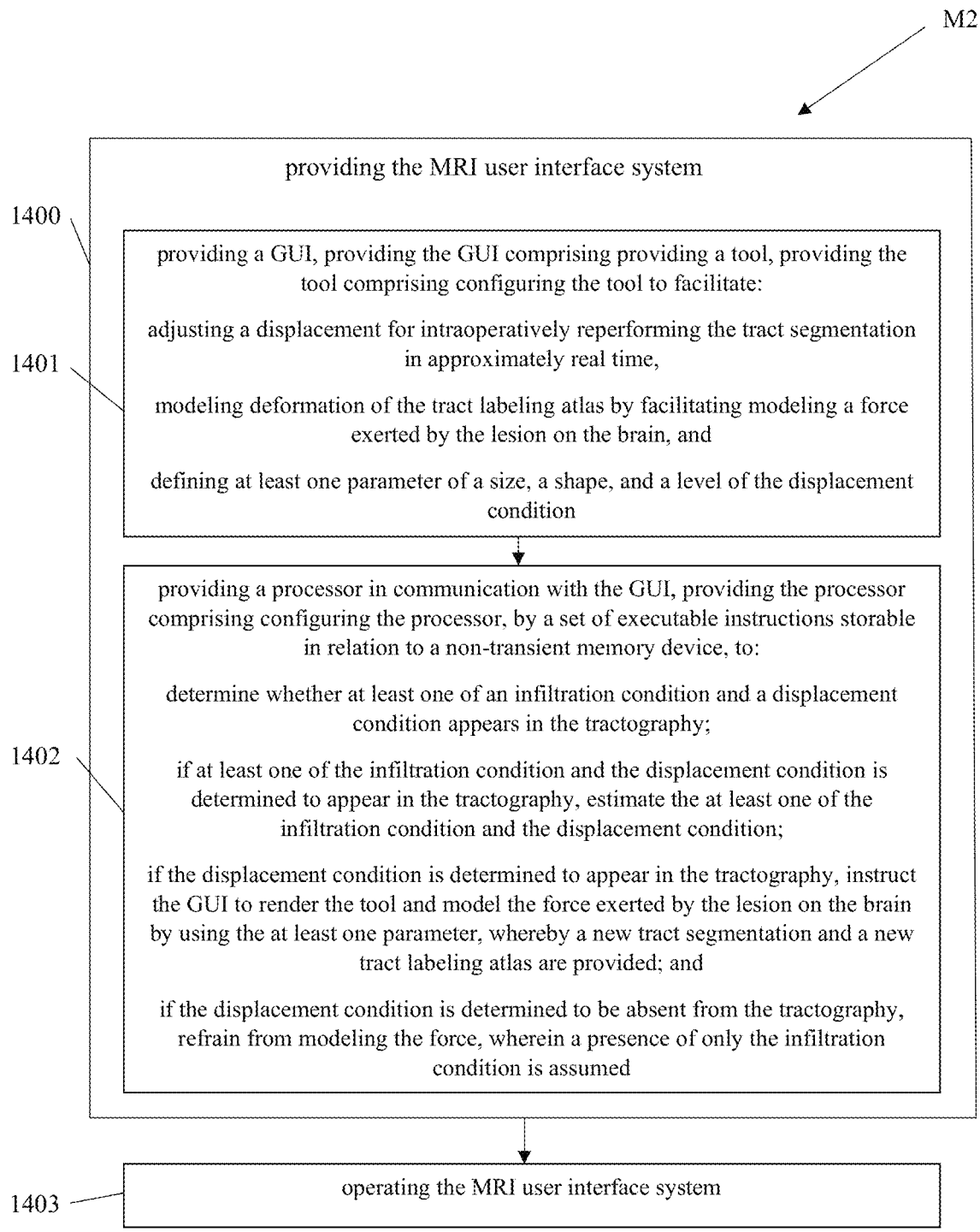
FIG. 14 is a flow diagram illustrating a method of labeling tractography from surgical planning data in a presence of a lesion in a brain, the tractography comprising a tract segmentation and a tract labeling atlas in relation to a three-dimensional space by way of an MRI user interface system.

Referring to FIG. 14, this flow diagram illustrates a method M2 of labeling tractography from surgical planning data in a presence of a lesion in a brain, the tractography comprising a tract segmentation and a tract labeling atlas in relation to a three-dimensional space by way of an MRI user interface system S, in accordance with an embodiment of the present disclosure. The method M2 comprises: providing the MRI user interface system S, indicated by block 1400, providing the MRI user interface system S comprising: providing a GUI 1201, e.g., the UI 80, providing the GUI comprising providing a tool, e.g., a slider feature 820 comprising a slider interface 830, providing the tool comprising configuring the tool to facilitate: adjusting a displacement for intraoperatively reperforming the tract segmentation in approximately real time, modeling deformation of the tract labeling atlas by facilitating modeling a force exerted by the lesion on the brain, and defining at least one parameter of a size, a shape, and a level of the displacement condition, as indicated by block 1401; and providing a processor in communication with the GUI, providing the processor comprising configuring the processor, by a set of executable instructions storable in relation to a non-transient memory device, to: determine whether at least one of an infiltration condition and a displacement condition appears in the tractography; if at least one of the infiltration condition and the displacement condition is determined to appear in the tractography, estimate the at least one of the infiltration condition and the displacement condition; if the displacement condition is determined to appear in the tractography, instruct the GUI to render the tool and model the force exerted by the lesion on the brain by using the at least one parameter, whereby a new tract segmentation and a new tract labeling atlas are provided; and if the displacement condition is determined to be absent from the tractography, refrain from modeling the force, wherein a presence of only the infiltration condition is assumed, as indicated by block 1402; and operating the MRI user interface system S, as indicated by block 1403.

Still referring to FIG. 14, in the method M2, providing the tool comprises providing a slider feature; and providing the slider feature comprises providing a slider. Providing the GUI comprises configuring the GUI to render a display of at least one of an object and a subject, the display showing at least one cross-sectional view, the at least one cross-sectional view comprising at least one view along at least one of three axes, and the three axes comprising a front to rear axis, a side to side axis, and a top to bottom axis. Providing the slider feature comprises providing a slider interface. Providing the slider interface comprises: providing a track for facilitating setting at least one of a size, a shape, and a level of displacement by a user, a representation of the lowest threshold value is disposed on a far left end of the track, and a representation of the highest value is disposed on a far right end of the track; and providing a position indicator configured to slide along the track, the position indicator comprising a thumb feature.

Still referring to FIG. 14, in the method M2, providing the slider interface further comprises providing at least one of: a value label disposed in relation to the position indicator, the value label configured to display at least one of a value corresponding to a position of the position indicator, the value represented as a numeral; a plurality of tick marks disposed along the track, the tick marks representing a plurality of predetermined values to which the position indicator movable; and a plurality of icons, the plurality of icons comprising a left end icon and a right end icon disposed at respective ends of the track to provide a visual representation of a range of threshold values, the left end icon indicating presence of a fully infiltrative disease condition, and, thus, no displacement, no force modeled, and no atlas deformation, and the right end icon indicating full mass effect, and, thus, displacement, a force modeled; and atlas deformation; and a button configured for trigger relabeling of the tractography.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor. A "module" can be considered as a processor executing computer-readable code.

A processor as described herein can be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, or microcontroller, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. In some embodiments, a processor can be a graphics processing unit (GPU). The parallel processing capabilities of GPUs can reduce the amount of time for training and using neural networks (and other machine learning models) compared to central processing units (CPUs). In some embodiments, a processor can be an ASIC including dedicated machine learning circuitry custom-build for one or both of model training and model inference. The disclosed or illustrated tasks can be distributed across multiple processors or computing devices of a computer system, including computing devices that are geographically distributed.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

The specific embodiments described above have been shown by way of example, and understood is that these embodiments may be susceptible to various modifications and alternative forms. Further understood is that the claims are not intended to be limited to the particular forms disclosed, but rather to cover all modifications, equivalents, and alternatives falling within the spirit and scope of this disclosure. While the foregoing written description of the system enables one of ordinary skill to make and use what is considered presently to be the best mode thereof, those of ordinary skill will understand and appreciate the existence of variations, combinations, and equivalents of the specific embodiment, method, and examples herein. The system should therefore not be limited by the above described embodiment, method, and examples, but by all embodiments and methods within the scope and spirit of the system. Thus, the present disclosure is not intended to be limited to the implementations shown herein but is to be accorded the widest scope consistent with the principles and novel features disclosed herein.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

INDUSTRIAL APPLICABILITY

Generally, the present disclosure industrially applies to surgical planning More specifically, the present disclosure industrially applies to surgical planning for neurosurgery. Even more specifically, the present disclosure industrially applies to labeling tractography from surgical planning data.

What is claimed:

1. An MRI user interface system for labeling tractography from surgical planning data in a presence of a lesion in a brain, the tractography comprising a tract segmentation and a tract labeling atlas in relation to a three-dimensional space, the system comprising:
   a graphical user interface (GUI) comprising a tool, the tool configured to facilitate: adjusting a displacement for intraoperatively reperforming the tract segmentation in real time, modeling deformation of the tract labeling atlas by facilitating modeling a force exerted by the lesion on the brain, and defining at least one parameter of a size, a shape, and a level of the displacement condition; and
   a processor in communication with the GUI and configured, by a set of executable instructions storable in relation to a non-transient memory device, to:
   determine whether at least one of an infiltration condition and a displacement condition appears in the tractography;
   if at least one of the infiltration condition and the displacement condition is determined to appear in the tractography, estimate the at least one of the infiltration condition and the displacement condition;
   if the displacement condition is determined to appear in the tractography, instruct the GUI to render the tool and model the force exerted by the lesion on the brain by using the at least one parameter, whereby a new tract segmentation and a new tract labeling atlas are provided; and
   if the displacement condition is determined to be absent from the tractography, refrain from modeling the force, wherein a presence of only the infiltration condition is assumed.

2. The system of claim 1, wherein the GUI is configured to render a display of at least one of an object and a subject, the display showing at least one cross-sectional view, the at least one cross-sectional view comprising at least one view along at least one of three axes, and the three axes comprising a front to rear axis, a side to side axis, and a top to bottom axis.

3. The system of claim 1, wherein the tool comprises a slider feature.

4. The system of claim 3, wherein the slider feature comprises a slider.

5. The system of claim 3, wherein the slider feature comprises a slider interface.

6. The system of claim 5, wherein the slider interface comprises:
   a track for facilitating setting at least one of a size, a shape, and a level of displacement by a user, a representation of the lowest threshold value is disposed on a far left end of the track, and a representation of the highest value is disposed on a far right end of the track; and
   a position indicator configured to slide along the track, the position indicator comprising a thumb feature.

7. The system of claim 6, wherein the slider interface further comprises at least one of:
   a value label disposed in relation to the position indicator, the value label configured to display at least one of a value corresponding to a position of the position indicator, the value represented as a numeral;
   a plurality of tick marks disposed along the track, the tick marks representing a plurality of predetermined values to which the position indicator movable; and
   a plurality of icons, the plurality of icons comprising a left end icon and a right end icon disposed at respective ends of the track to provide a visual representation of a range of threshold values, the left end icon indicating presence of a fully infiltrative disease condition, and, thus, no displacement, no force modeled, and no atlas deformation, and the right end icon indicating full mass effect, and, thus, displacement, a force modeled; and atlas deformation; and
   a button configured for trigger relabeling of the tractography.

8. A method of providing an MRI user interface system for labeling tractography from surgical planning data in a presence of a lesion in a brain, the tractography comprising a tract segmentation and a tract labeling atlas in relation to a three-dimensional space, the method comprising:
   providing a graphical user interface (GUI), providing the GUI comprising providing a tool, providing the tool comprising configuring the tool to facilitate: adjusting a displacement for intraoperatively reperforming the tract segmentation in real time, modeling deformation of the tract labeling atlas by facilitating modeling a force exerted by the lesion on the brain, and defining at least one parameter of a size, a shape, and a level of the displacement condition; and
   providing a processor in communication with the GUI, providing the processor comprising configuring the processor, by a set of executable instructions storable in relation to a non-transient memory device, to:
   determine whether at least one of an infiltration condition and a displacement condition appears in the tractography;
   if at least one of the infiltration condition and the displacement condition is determined to appear in the tractography, estimate the at least one of the infiltration condition and the displacement condition;
   if the displacement condition is determined to appear in the tractography, instruct the GUI to render the tool and model the force exerted by the lesion on the brain by using the at least one parameter, whereby a new tract segmentation and a new tract labeling atlas are provided; and
   if the displacement condition is determined to be absent from the tractography, refrain from modeling the force, wherein a presence of only the infiltration condition is assumed.

9. The method of claim 8, wherein providing the GUI comprises configuring the GUI to render a display of at least one of an object and a subject, the display showing at least one cross-sectional view, the at least one cross-sectional view comprising at least one view along at least one of three axes, and the three axes comprising a front to rear axis, a side to side axis, and a top to bottom axis.

10. The method of claim 8, wherein providing the tool comprises providing a slider feature.

11. The method of claim 10, wherein providing the slider feature comprises providing a slider.

12. The method of claim 10, wherein providing the slider feature comprises providing a slider interface.

13. The method of claim 12, wherein providing the slider interface comprises:
   providing a track for facilitating setting at least one of a size, a shape, and a level of displacement by a user, a representation of the lowest threshold value is disposed on a far left end of the track, and a representation of the highest value is disposed on a far right end of the track; and providing a position indicator configured to slide along the track, the position indicator comprising a thumb feature.

14. The method of claim 13, wherein providing the slider interface further comprises providing at least one of:
a value label disposed in relation to the position indicator, the value label configured to display at least one of a value corresponding to a position of the position indicator, the value represented as a numeral;
a plurality of tick marks disposed along the track, the tick marks representing a plurality of predetermined values to which the position indicator movable; and
a plurality of icons, the plurality of icons comprising a left end icon and a right end icon disposed at respective ends of the track to provide a visual representation of a range of threshold values, the left end icon indicating presence of a fully infiltrative disease condition, and, thus, no displacement, no force modeled, and no atlas deformation, and the right end icon indicating full mass effect, and, thus, displacement, a force modeled; and atlas deformation; and
a button configured for trigger relabeling of the tractography.

15. A method of labeling tractography from surgical planning data in a presence of a lesion in a brain, the tractography comprising a tract segmentation and a tract labeling atlas in relation to a three-dimensional space by way of an MRI user interface system, the method comprising:
providing the MRI user interface system comprising:
providing a graphical user interface (GUI), providing the GUI comprising providing a tool, providing the tool comprising configuring the tool to facilitate: adjusting a displacement for intraoperatively reperforming the tract segmentation in real time, modeling deformation of the tract labeling atlas by facilitating modeling a force exerted by the lesion on the brain, and defining at least one parameter of a size, a shape, and a level of the displacement condition; and
providing a processor in communication with the GUI, providing the processor comprising configuring the processor, by a set of executable instructions storable in relation to a non-transient memory device, to: determine whether at least one of an infiltration condition and a displacement condition appears in the tractography; if at least one of the infiltration condition and the displacement condition is determined to appear in the tractography, estimate the at least one of the infiltration condition and the displacement condition; if the displacement condition is determined to appear in the tractography, instruct the GUI to render the tool and model the force exerted by the lesion on the brain by using the at least one parameter, whereby a new tract segmentation and a new tract labeling atlas are provided; and if the displacement condition is determined to be absent from the tractography, refrain from modeling the force, wherein a presence of only the infiltration condition is assumed; and
operating the MRI user interface system.

16. The method of claim 15, wherein providing the GUI comprises configuring the GUI to render a display of at least one of an object and a subject, the display showing at least one cross-sectional view, the at least one cross-sectional view comprising at least one view along at least one of three axes, and the three axes comprising a front to rear axis, a side to side axis, and a top to bottom axis.

17. The method of claim 15, wherein providing the tool comprises providing a slider feature.

18. The method of claim 17, wherein providing the slider feature comprises providing a slider.

19. The method of claim 17, wherein providing the slider feature comprises providing a slider interface.

20. The method of claim 19,
wherein providing the slider interface comprises:
providing a track for facilitating setting at least one of a size, a shape, and a level of displacement by a user, a representation of the lowest threshold value is disposed on a far left end of the track, and a representation of the highest value is disposed on a far right end of the track; and
providing a position indicator configured to slide along the track, the position indicator comprising a thumb feature, and
wherein providing the slider interface further comprises providing at least one of:
a value label disposed in relation to the position indicator, the value label configured to display at least one of a value corresponding to a position of the position indicator, the value represented as a numeral;
a plurality of tick marks disposed along the track, the tick marks representing a plurality of predetermined values to which the position indicator movable; and
a plurality of icons, the plurality of icons comprising a left end icon and a right end icon disposed at respective ends of the track to provide a visual representation of a range of threshold values, the left end icon indicating presence of a fully infiltrative disease condition, and, thus, no displacement, no force modeled, and no atlas deformation, and the right end icon indicating full mass effect, and, thus, displacement, a force modeled; and atlas deformation; and
a button configured for trigger relabeling of the tractography.

* * * * *